United States Patent [19]
Tachi

[11] Patent Number: 5,108,360
[45] Date of Patent: Apr. 28, 1992

[54] MONITORING SYSTEM FOR MEDICAL PUMP

[75] Inventor: Hiroyuki Tachi, Tokyo, Japan

[73] Assignees: Aisin Seiki Kabushiki Kaisha, Kariya; Kabushiki Kaisha Shinsangyokaihatsu, Tokyo, both of Japan

[21] Appl. No.: 500,150

[22] Filed: Mar. 28, 1990

[30] Foreign Application Priority Data

| Mar. 31, 1989 | [JP] | Japan | 1-82043 |
| Mar. 31, 1989 | [JP] | Japan | 1-82044 |
| Mar. 31, 1989 | [JP] | Japan | 1-82045 |
| Mar. 31, 1989 | [JP] | Japan | 1-82046 |
| Mar. 31, 1989 | [JP] | Japan | 1-82047 |

[51] Int. Cl.$^5$ .................................................. A61M 1/12
[52] U.S. Cl. .................................................. 600/16; 623/3
[58] Field of Search .......................... 600/16, 17; 623/3

[56] References Cited

U.S. PATENT DOCUMENTS

| 3,430,624 | 3/1969 | Flanagan et al. | 600/17 |
| 3,465,746 | 9/1969 | Guarino | 600/17 |
| 3,966,358 | 6/1976 | Heimes et al. | 623/3 |
| 4,231,354 | 11/1980 | Kurtz et al. | 600/17 |
| 4,597,381 | 7/1986 | Oumi et al. | 600/16 |
| 4,687,424 | 8/1987 | Heimes | 623/3 |
| 4,775,887 | 10/1988 | Tachi | 600/16 |
| 4,865,581 | 9/1989 | Lundquist et al. | 600/17 |

Primary Examiner—William E. Kamm
Assistant Examiner—Kennedy J. Schaetzle
Attorney, Agent, or Firm—Burns, Doane, Swecker & Mathis

[57] ABSTRACT

A monitoring system for a medical pump having a reversible operating body for compressing/expanding a space for accommodating a fluid, suction/ejection ports communicating via a no-return valve with this space and units for driving the reversible operating means. The system comprises modules for informing abnormalities in the case of a stoppage for predetermined period at a top or bottom dead center of the reversible operating body, or when this body does not traverse predetermined positions, or when the top or bottom dead center exceeds limit positions, or when a centroidal position of the reversible operating body deviates from a set range, and a module for measuring a flow rate of the blood ejected from the artificial heart by calculating an internal volume of the reversible operating body from the images photographed.

2 Claims, 21 Drawing Sheets

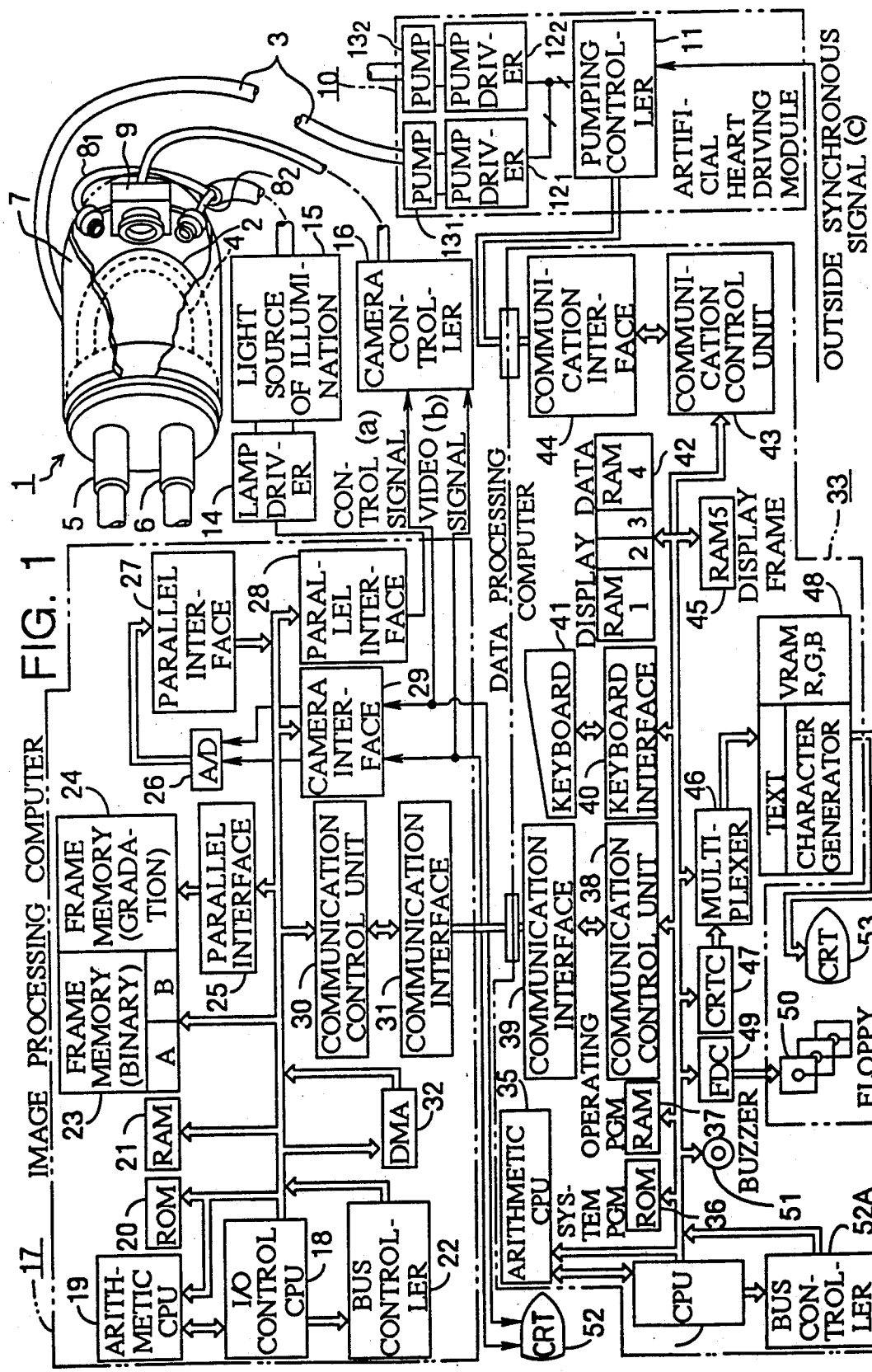

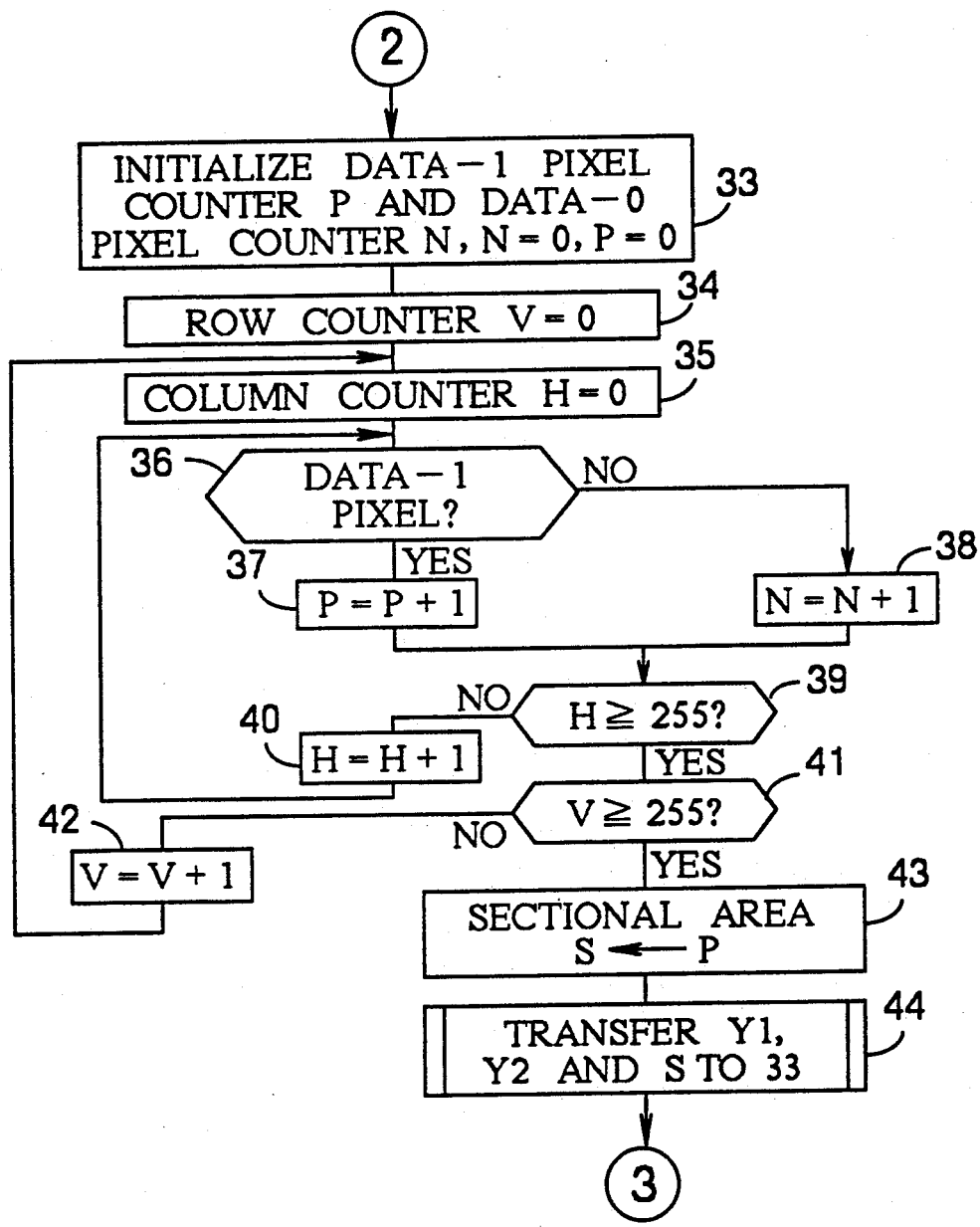

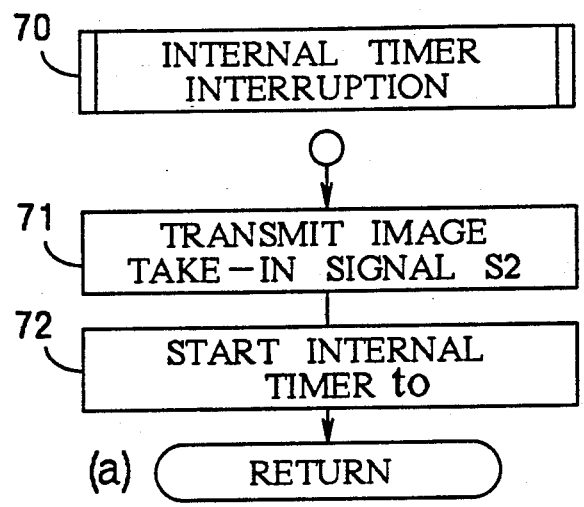
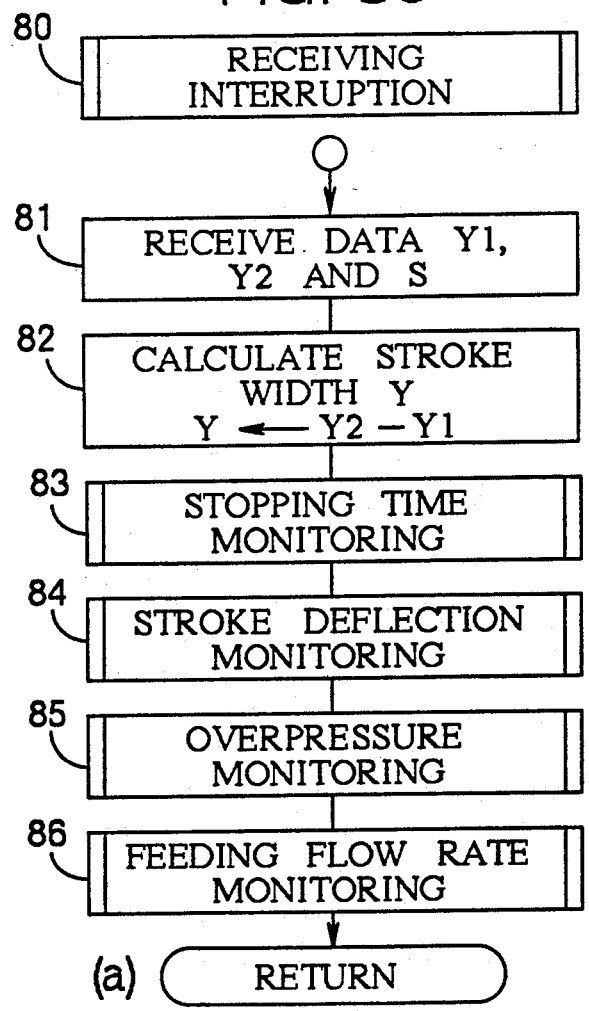

(a) ONE-DIMENSIONAL ARRAYS A, B AND C

A | 0 | 1 | 2 | 3 | 4 | ..... | 149 |

B | 0 | 1 | 2 | 3 | 4 | ..... | 148 |

C | 0 | 1 | 2 | 3 | .... | 15 |

FIG. 9c
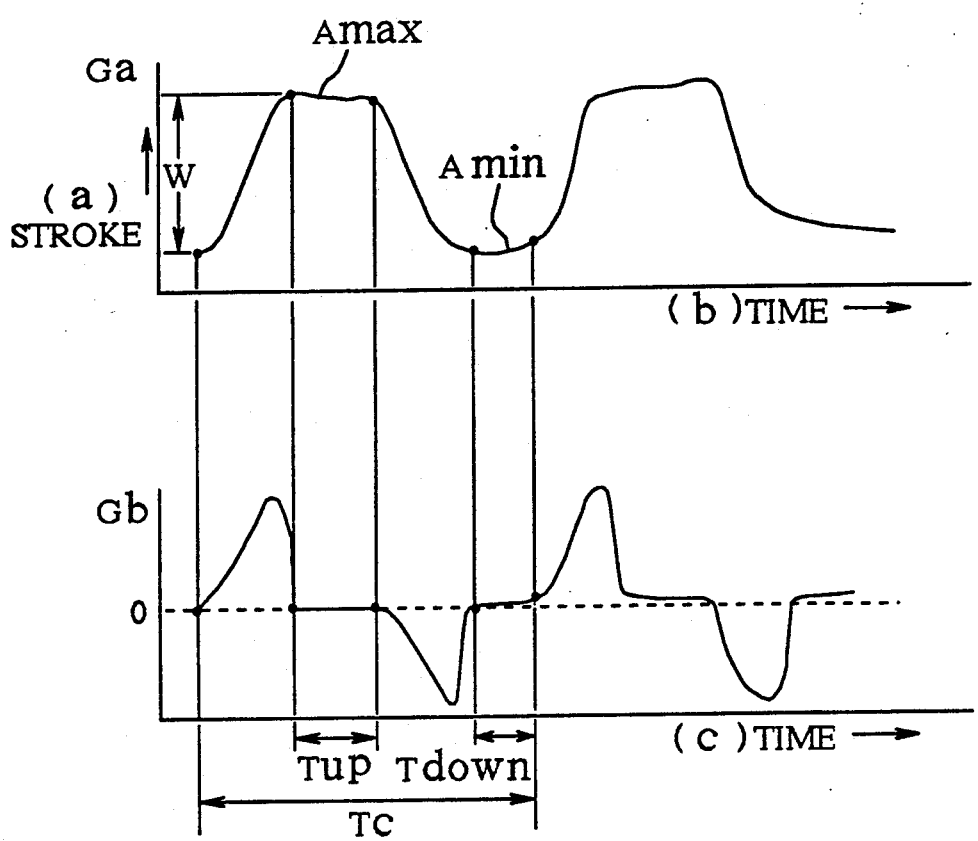
(d) IF Tup > Tdown, STROKE WIDTH(W) IS INVARIABLE EVEN WHEN REDUCING TC BY A TIME OF Tdown
TupD = Tup − Tdown
TCD = TC − 2Tdown
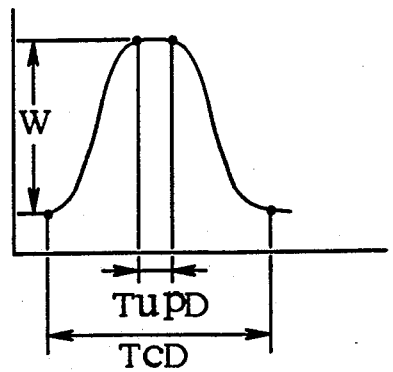

MONITORING SYSTEM FOR MEDICAL PUMP

BACKGROUND OF THE INVENTION

The present invention is directed generally to a medical pump for feeding a fluid to a living body and/or pumping or discharging the fluid therefrom and more particularly, though not intended for a limit to this, to an artificial heart, serving as a substitute for a vital heart or as an auxiliary to the vital heart, for circulating blood in vivo.

Whether the operation of, e.g., an artificial heart is correct or not is of much significance in a medical sense. The artificial heart has a rated range of a stroke width in terms of structure. If driven in excess of this range, the artificial heart will undergo serious damages in structure, which probably gives a remarkable hazard to the living body to which the artificial heart is connected. The hazardous situation is derived from an excessive expansion of the discharge passage on one hand and an excessive collapse on the other hand.

The overexpansion causes the discharge to impinge and rub on a casing, with the result that it will be worn away due to a long stretch of use and presumably eventually ruptured. Whereas in the case of the overcollapse, an overload is applied on a driving module for driving the artificial heart, and the driving module is thereby damaged electrically or mechanically. The overcollapse also presents a high probability that erythrocytes will be destroyed in addition to abrasion caused by rubbing the inner surfaces against each other. Hence, a system for monitoring operational conditions thereof is required. It is a common practice that an image of a reversible operating body of the artificial heart is displayed on a monitor TV by incorporating a small-sized video camera like a CCD camera into the artificial heart. In order to help monitoring only by visual observation, a monitoring system disclosed in Japanese Patent Application No. 62839/1987 is constituted such that movement of the blood is photographed by means of a CCD camera in time series to accumulate the images thereof which are then partly extracted, and these images are arranged in a direction of a time axis to exhibit variations with a passage of time. In this type of monitoring system also, the correctness or incorrectness of the operation and an availability or unavailability of increase in blood flow rate have to be judged by visually confirming the images. It is therefore difficult to make a judgment from the images formed by photographing the operating body. Besides, a misjudgment tends to be made.

In the above-described monitoring system, the operator likewise has to judge an adequateness or inadequateness of the blood flow rate through his visual recognition of the images. The judgment from the images of the operating body is effected with difficulty.

Parts of the artificial heart, which are brought into contact with the blood, undergo an antithrombotic treatment to prevent thrombus. The blood flows at an adequate velocity under normal using conditions, and there is caused no blood stagnation in contact portions of a blood pump with the blood, thereby producing no thrombus. It is because blood platelets are not activated. However, if a flow rate of the blood from the artificial heart is extremely small; or a stroke per heartbeat is small; or an interval between one heartbeat and the next heartbeat is too long even when the stroke suffices, the blood becomes stagnant locally, and a time for which the blood stops in some parts of the discharge passage of the artificial heart. This phenomenon increases the probabilities that the platelets tend to be activated in those portions to facilitate the generation of thrombus, and the activated platelets spread over respective parts of the living body to clog peripheral blood vessels. For this reason, there are set a minimum flow rate under which the amount of flowing blood should not decrease, a least stroke and a maximum pulsation interval in the artificial heart.

If the passage for removing the blood from the living body and ejecting it therethrough is abnormally deformed, a blood pumping flow rate fluctuates. In addition, a local stagnation of the blood is produced in the suck, where the platelets are activated to cause the thrombus at a high probability. Simultaneously, stress locally acts on the suck, resulting in a breakage after a long period of time. Where the passage abnormally deflects, similar problems arise. The artificial heart continues to be employed for a relatively long period of time, and hence the above-mentioned system for monitoring the artificial heart is needed. The monitoring system is capable of judging an abnormal deformation, an abnormal deflection and a rupture of the suck by visually recognizing time-series configurational variations in the passage image. In this monitoring system also, the operator is required to judge the correctness or incorrectness of the suck operation through his visual recognition of the images. It is similarly difficult to make a judgment from the images obtained by photographing the operating body. A misjudgment is likely to be made.

An arrangement of a monitoring system disclosed in Japanese Patent Laid-Open Publication No. 158864/1985 is that a passage thickness is measured by making use of a Hall element preparatory to conversion into a passage volume, and a flow rate of blood is calculated from variations in the volume which are based on time-series changes in passage thickness.

According to the monitoring system disclosed in Japanese Patent Laid-Open Publication No. 158864/1985, a flow rate of the blood ejected by the artificial heart is automatically measured without relying on the judgment by visual observation of the operator, and it follows that the operator does not have to presume the flow rate of the ejected blood. The flow rate of the ejected blood, however, depends on conditions of the living body to which the artificial heart is connected as well as on a driving cycle and a driving pressure of the artificial heart. In other words, there are cases where the blood flow rate increases but does not rise particularly when intensifying a drive of the artificial heart. Hence, even if the flow rate of the ejected blood is automatically calculated by measuring the suck thickness in time series, the operator is unable to know whether the flow rate of the ejected blood should be increased or reduced.

According to the foregoing monitoring system, a flow rate of the blood ejected from the artificial heart is automatically measured without relying on the judgment by visual observation of the operator, whereby the operator does not have to presume the flow rate of the ejected blood. The properness or unproperness thereof can be determined from the blood flow rate. However, even when the artificial heart ejects the blood whose amount is greater than a minimum flow rate at which, for example, the platelets are not virtually activated, and if the passage biases on an expanding or contracting side in consequence of its stroke deviating from a normal range, an operating state of the passage varies, and the blood is apt to stagnate partially in the passage. Based on the method of measuring the flow rate by means of the monitoring system disclosed in Japanese Patent Laid-Open Publication No. 158864/1985, it is impossible to detect or judge an abnormality in such an operating state.

In the above-mentioned monitoring system, the overexpansion or overcollapse of the passage can not automatically be detected. Therefore, the operator has hitherto monitored directly the artificial heart or indirectly through a monitor camera by the visual observation. To be specific, the operator judges the overexpansion or overcollapse in an intellectual manner by visually recognizing a configuration of the pulsating passage. Such a monitoring operation, however, requires a good deal of labor, because the operation has to continue during a period for which the artificial heart works, as a result of which a judgment error or a monitoring mistake is likely to take place.

In the monitoring system described above, if the Hall element is equipped apart from the passage, the measurement by the Hall element becomes inaccurate, because variations in the passage thickness are small. This in turn makes a measurement value of the flow rate inaccurate. When mounting the Hall element on the passage, relatively precise measurement may be attained. It is, however, considerably difficult to mount the Hall element on the passage. Besides, there arise problems in which expanding/contacting characteristics of the passage change, and the excessive stress is applied locally on the passage, resulting in a decline of its durability.

In the aforementioned monitoring system, it is unfeasible to directly monitor an abnormal deformation, an abnormal deflection and a rupture of the passage. It is a large burden on the operator to monitor directly the artificial heart all the time or indirectly via a monitor TV, and at the same time there is a high probability that a misjudgment or monitoring mistake is to be caused.

SUMMARY OF THE INVENTION

It is a primary object of the present invention, which has been devised to obviate the foregoing defects inherent in the prior arts, to provide medical pump monitoring systems for automatically generating information by which to know whether a flow rate of ejected blood can be increased or not, automatically informing a stroke biasing abnormality of the reversible operating means of the medical pump, automatically detecting and informing an overdrive abnormality of the reversible operating means thereof, detecting a fluid flow rate while being in non-contact with a fluid in a fluid accommodating space defined by the reversible operating means by relatively accurately detecting displacement of the reversible operating means while being in non-contact therewith, and automatically detecting and informing an abnormal deformation, an abnormal deflection and a breakage of the reversible operating means.

To this end, according to one aspect of the invention, there is provided a monitoring system for a medical pump having: a reversible operating means for compressing/expanding a space for accommodating a fluid; a discharge port and a suction port which communicate via a non-return valve with the fluid accommodating space; and reversible driving means for driving the reversible operating means, the system comprising: dead center detecting means for detecting at least one of top and bottom dead centers of the reversible operating means; a dead center stopping time measuring means for measuring a time for which the dead center detecting means continue to detect the dead center; and an informing means for informing the time measured by the dead center stopping time measuring means.

According to another aspect of the invention, there is provided a monitoring system for a medical pump having: a reversible operating means for compressing/expanding a space for accommodating a fluid; a discharge port and a suction port which communicate via a non-return valve with the fluid accommodating space; and reversible driving means for driving the reversible operating means, the system comprising: a stroke detecting means for detecting at least one of discharge and suction strokes of the reversible operating means; a passage detecting means for detecting whether or not a stroke detected by the stroke detecting means traverses predetermined strokes between a set top dead center and a set bottom dead center of the reversible operating means; and an informing means for giving abnormality information in response to a negative result of the detection by the passage detecting means.

According to still another aspect of the invention, there is provided a monitoring system for a medical pump having: a reversible operating means for compressing/expanding a space for accommodating a fluid; a discharge port and a suction port which communicate via a non-return valve with the fluid accommodating space; and reversible driving means for driving the reversible operating means, the system comprising: dead center detecting means for detecting at least one of top and bottom dead centers of the reversible operating means; a passage detecting means for detecting whether or not the dead centers detected by the dead center detecting means exceed set limit points; and an informing means for giving abnormality information in response to an excessive value detected by the passage detecting means.

According to a further aspect of the invention, there is provided a monitoring system for a medical pump having: a reversible operating means for compressing/expanding a space for accommodating a fluid; a discharge port and a suction port which communicate via a non-return valve with the fluid accommodating space; and reversible driving means for driving the reversible operating means, the system comprising: an imaging means for generating image information by photographing the reversible operating means; an image pick-out means for picking out an image of the reversible operating means from the image information generated by the imaging means; a converting means for converting configurational parameters of the image of the reversible operating means which has been picked out by the image pick-out means into a volumetric capacity of a fluid accommodating space defined by the reversible operating means; a variation rate detecting means for detecting a variation rate of the volumetric capacity converted by the converting means; an integrating means for integrating the variation rate detected by the variation rate detecting means; and an informing means for informing a value proportional to a value obtained by effecting the integration by the integrating means.

According to a still further aspect of the invention, there is provided a monitoring system for a medical pump having: a reversible operating means for compressing/expanding a space for accommodating a fluid; a discharge port and a suction port which communicates via a non-return valve with the fluid accommodating space; and reversible driving means for driving the reversible operating means, the system comprising an imaging means for generating image information by photographing the reversible operating means; an image pick-out means for picking out an image of the reversible operating means from the image information generated by the imaging means; a centroid detecting means for calculating a centroidal position of the image of the reversible means which has been picked out by the image pick-out means; a centroidal deviation detecting means for detecting whether or not the centroidal position calculated by the centroid detecting means fall within a set range; and an informing means for giving corresponding information in response to a negative result of the detection by the centroidal deviation detecting means.

The following functiosn are characteristic of a monitoring system for a medical pump according to the present invention. If the top or bottom dead center measured by the dead center stopping time measuring means is long, a flow rate of an ejected fluid is augmented by increasing the nubmer of heartbeats of the artificial heart. The fact that the stopping time is excessively long implies a failure, an abnormality just before the stoppage and a stop abnormality. According to this monitoring system, the informing means informs the operator of a stopping time, whereby the operator is able to judge an availablity or unavailability of increase in the flow rate of the ejected fluid and also the abnormalities in the artificial heart.

When the reversible operating means of the medical pump oerates with strokes between the set top and bottom dead centers—i.e., when the reversible operating means operates to traverse predetermined strokes, no stagnation of the fluid is produced. (a) When the stroke of the reversible operating means is reduced, the flow rate decreases, and the stagnation is thereby caused with facility. (b) If the stroke of the reversible operating means is baised on the expanding or contracting side, the local stagnation tends to be produced in the fluid space sectioned by the reversible operating means. The monitoring system is also arranged such that the stroke detecting means serves to detect the strokes of the reversible operating means, while the passage detecting means detects whether the stroke detected by the stroke detecting means traverses the predetermined stroke. If the detected result is negative, the informing means informs the operator of an abnormality. In both cases (a) and (b), the abnormality information is imparted automatically from the informing means. With this arrangement, there are automatically informed the stroke bias and the local fluid stagnation derived therefrom, which can not automatically be noticed on the basis of the measurement of blood flow rate by the monitoring system disclosed in Japanese Patent Laid-Open Publication No. 58864/1985.

The reversible oprating means of the medical pump moves with an excessive expansion or contraction, as a result of which the stroke dead centers of the reversible operating means which are detected by the dead center detecting means exceed set limit points. The passage detecting means detects this excess, and the informing means issues the abnormality information in response to this detection. The operator is able to know the abnormal condition without constantly monitoring the reversible operating means, thereby reducing the labors required for monitoring. Moreover, the probability that an error in judgement and of a monitoring mistake can considerably be decreased.

A configurational parameter of the image of the reversible operating means which has been formed by the imaging means and picked out by the image pick-out means, i.e., a volumetric capacity of the fluid accommodating space defined by the reversible operating means with respect to, for instance, a width or an area exhibits a one-to-one relationship. Based on this relationship, the converting means calculates the volume of the fluid accommodating space. On the other hand, the variation rate detecting means detects a variation rate of the volume, and the integrating means integrates the variation rate. The integrated values are conceived as a volume variation quantity of the fluid accommodating space sectioned by the reversible operating means for a period from a start of the integration to an end thereof and as an amount of the fluid ejected by the reversible oeprating means. A flow rate is given by a fluid quantity/time. The informing means informs values proportional to the integrated values. These proportional values are flow rates or values proportional thereto. The flow rates or flow rate corresponding values are informed from the informing means. The imaging means is disposed in non-contact with the reversible operating means, and hence there is caused no variation in its operating property and no drop in its durability because of the arrangment that the reversible operating means has no element added. Owing to imaging means and image processing techniques of nowadays, the images of the reversible operating means can accurately be extracted, and a configurational parameter thereof can also exactly be detected. Consequently, the flow rate informed from the informing means becomes precise.

If an abnormal deformation, an abnormal deflection and a rupture are produced in the reversible operating means, the centroidal position of an image of the reversible operating means which has been photographed by the imaging mens and picked out by the image pick-out means deviates from the centroidal position at the time of normal operation, viz., from a set range. In this case, the centroidal deviation detecting means behaves to detect the centroidal deviation, and correspondingly the informing means issues information about the detection. The abnormal deformation and deflection appear before the reversible operating means is ruptured, at which time the informing means informs the oeprator of the abnormalities. Therefore, the abnormality notice is issued before the breakage of the reversible operating means. The operator visually inspects the medical pump with confirmation in response to the abnormality information. If the pump is abnormal, the medical pump may be replaced. Whereas if normal, the alternative is to adjust a driving pressure of a pump driving module or to check a failure of this driving module or to replace it. The operator is not required to monitor the motions of the medical pump all the time, resulting in reductions both in working burden and in possibility where a judgment error and a monitoring mistake are to be produced.

BRIEF DESCRIPTION OF THE DRAWINGS

Other objects and advantages of the present invention will become apparent during the following discussion taken in conjunction with the accompanying drawings, in which:

FIG. 1 is a block diagram illustrating one embodiment of a monitoring system for a medical pump according to the present invention;

FIGS. 2a to 2c are flowcharts each showing control operations of CPU18 depicted in FIG. 1;

FIGS. 3a to 3c, 4a, 4b and 5 through 8 are flowcharts each showing control operations of CPU 34 depicted in FIG. 1;

FIG. 9c is a graphic chart depicting a transition Ga of the stroke Y of the passage 4, a transition Gb of a differential value of the stroke Y and a transition of the stroke y when diminishing the stopping time;

DESCRIPTION OF THE PREFERRED EMBODIMENTS

Figure 2A:
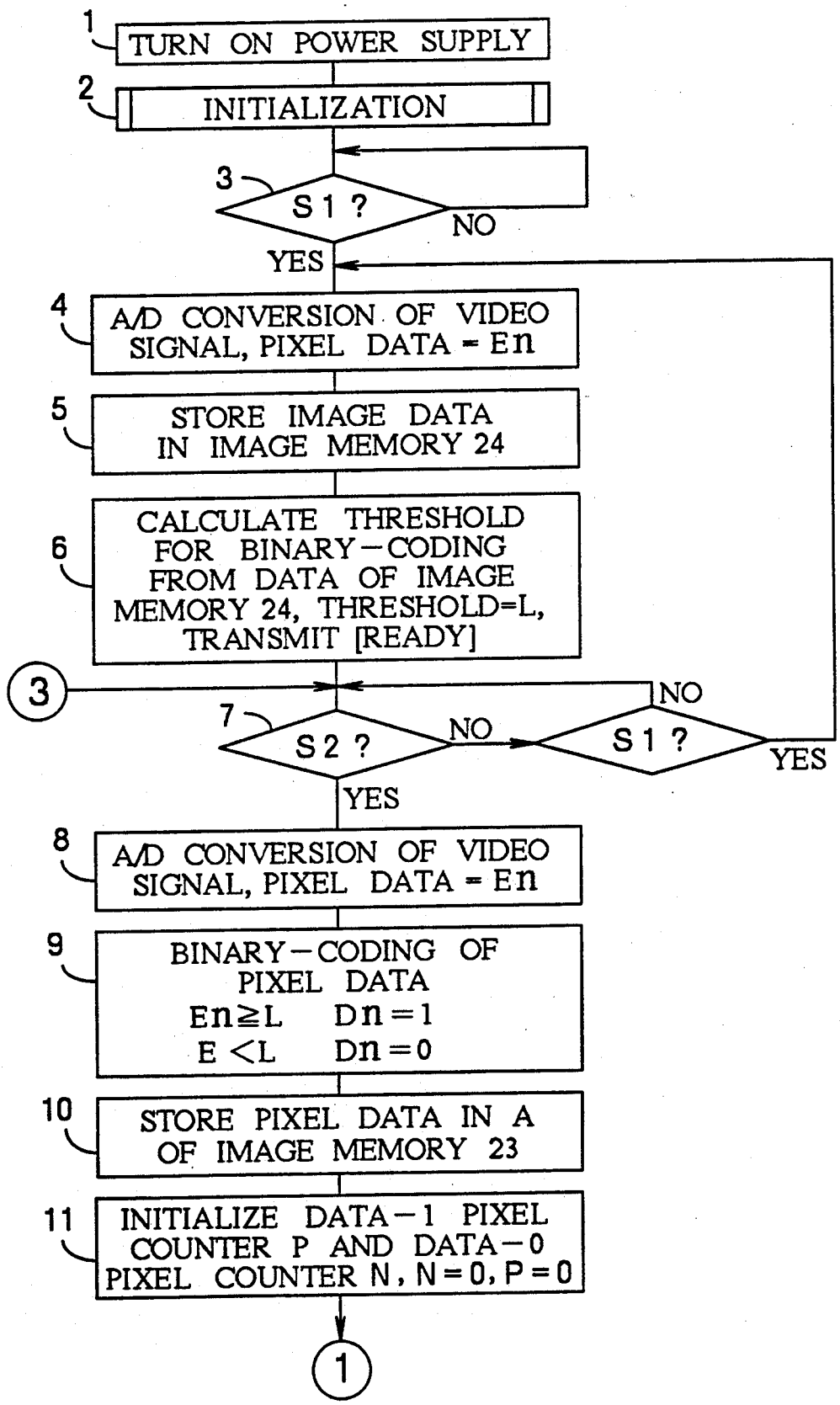

A preferred embodiment of the monitoring system for a medical pump of the present invention will hereinafter be described with reference to the accompanying drawings.

Turning first to FIG. 1, there is illustrated one embodiment of the monitoring system of the invention. interposed between an inner space of a flexilble passage 4 of an artificial heart 1 and an output port 5 is a non-return valve which admits an outflow (ejection) of a fluid from the inner space of the passage 4 to the output port 5 but cuts off the fluid flowing in a direction reverse thereto. Interposed between the inner space of the passage 4 and a suction port 6 is a non-return valve which admits an inflow (suction) of the fluid from the suction port 6 to the inner space of the passage 4 but cuts off the fluid flowing in a direction opposte thereto. The flexible passage 4 is covered with a transparent internal casing 2.

Provided outwardly of the internal casing 2 is an external casing 7 to which light projection ends of optical fibers $8_1$ and $8_2$ and also a CCD camera 9 are fixed. The CCD camera 9 is located on the extension of line of a major axis of the passage 4, a visual field of which is set to accommodate the whole passage 4 including its trail end into a frame. The light projection ends of the optical fibers $8_1$ and $8_2$ are so set that when viewed from the camera 9, an entire outer surface of the passage 4 is illuminated.

A tube 3 communicating with the inner space of the transparent internal casing 3 is connected to an operating fluid driving pump $13_1$ of an artificial hear driving module 10. The pump $13_1$ alternately imparts a high pressure and a low pressure through an operating fluid (a gas like air in the case of, e.g., Japanese Patent Application No. 85084/1987, or a liquid like silicon oil in the case of, e.g., Japanese Patent Application No. 25371/1989) via the tube 3. The operating fluid driving pump $13_1$ is electrified by means of a pump driver $12_1$. A discharge electrifying duty (discharge period/(discharge period+suction period)×100%) at one beat of discharge/suction of the pump driver $12_1$ is determined by a pumping controller 11 on the basis of set data given from a data processign computer 33. The pumping controller 11, when an asynchronous mode is instructed from the data processing computer 33, drives the pump $13_1$ at beats a cycle Tc and a duty (Tp/Tc×100% which are specified by the computer 33 in the controller 11. If an outside synchronous mode is instructed, the controller 11 acts to drive the pimp $13_1$ at beats synchronizing with synchronous signals (beat pulses of a living body) transmitted from an electrocardiograph or the like. In an illustrative example, the artificial heart driving module 10 are constituted to simultaneously control two pieces of artificial hearts (right and left). One artificial heart not illustrated receives high/low pressures given from a pump $13_2$ through an operating fluid, while a pump driver $12_2$ electrifies the pump $13_2$.

The CCD camera 9 connected to a camera controller 16 transmits video signals (analog image signals) to the controller 16. The controller 16 in turn imparts the video signals to a CRT display 52 and an image processing computer 17. Images of the passage 4 are momentarily displayed on CRT 52.

The image processing computer 17 behaves to convert the video signals into digital data (gradation data) per frame and write the digital data to a frame memory 24. After writing the data for one frame, the gradation data are binary-coded for conversion into image signals (1 bit for 1 dot: 1 represents black, and 0 represents white). The thus converted image signals are written to A of the frame memory 23. The subsequent step is to calculate an address Y1 of an upper fringe of an image of the passage 4 and an address Y2 of a lower fringe thereof in a vertical direction V on the image frame (a picture of the CCD camera). An area S (a portion indicated by oblique lines in FIG. 9a) of the image of the suck 4 is also computed. The thus calculated addresses Y1 and Y2 and the area S are sent to a data processing computer 33.

The data processing computer 33 serves to give a pumping controller 11 operating condition set data Tc, Tp and asychronous/synchronous modes inputted through a keyboard 41, thereby setting driving conditions of the artificial heat 1. Simultaneously, the computer 33 reads monitor judging condition data (SA, SB, IT, Smax, Smin, Vol=f(Y), and centroidal position) inputted via the keyboard 41 and sets the data inside a register. Based on the addresses Y1 and Y2 and the area S which are imparted from the image processing computer 17 as well as on the set monitor judging conditions, indices indicating the operating states of the passage 4 are calculated, and adequateness or inadequateness of the operating states is obtained by computation. The results are displayed on the CRT display 53.

Figure 2B:
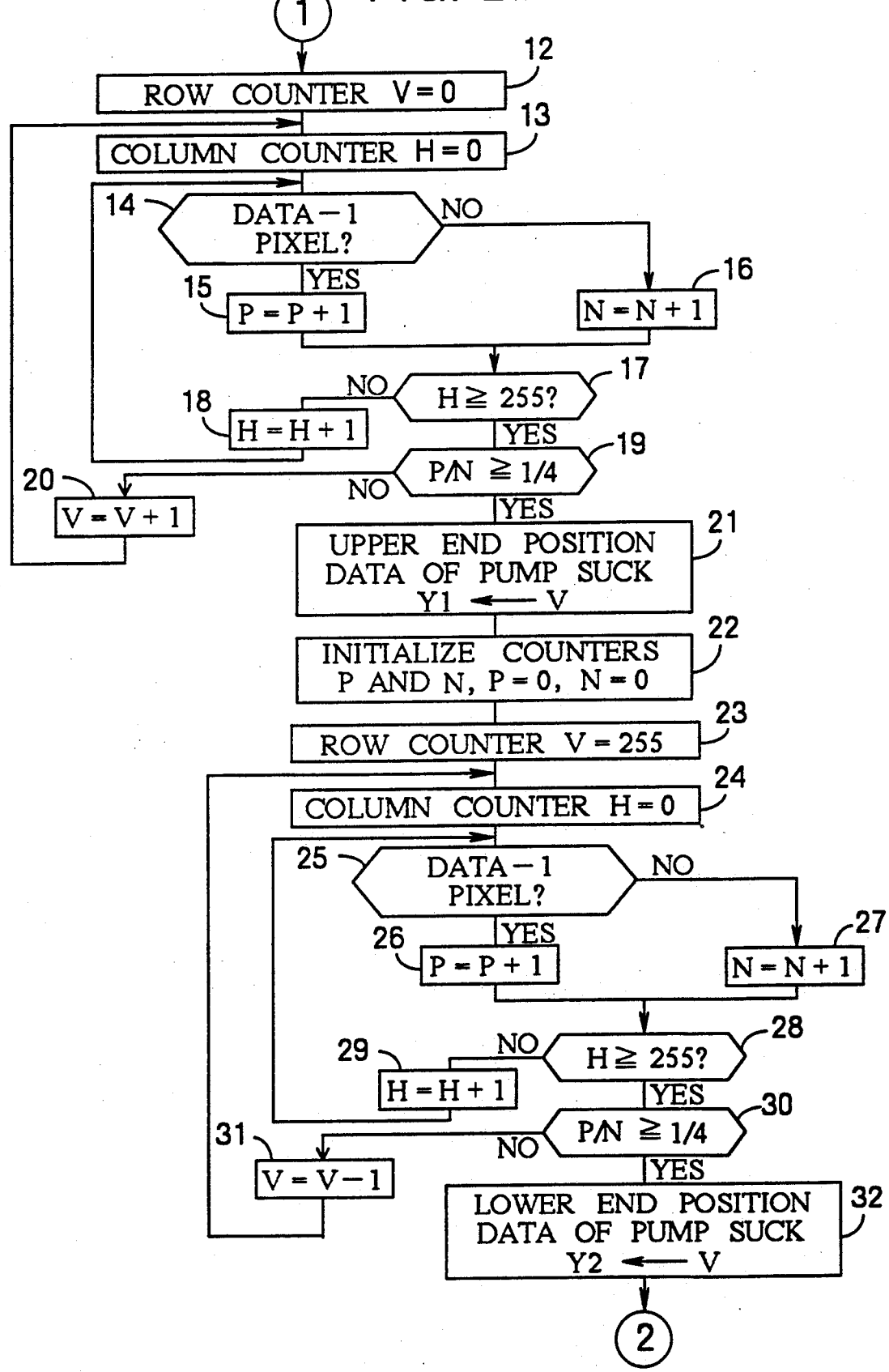

Turning attention to FIGS. 3a through 8, there are shown control operations executed by CPUs 34 and 35 of the data processing computer 33. FIGS. 2a to 2c illustrates control operations executed by CPUs 18 and 19 of the image processing computer 17.

The control operation of CPU 34 of the data processing computer 33 will first be described with reference to FIGS. 3a through 3c. When making a current of a power supply (a step 51: the term "step" will hereinafter be omitted in brackets), CPU 34 sets an I/O port at a signal level when being in a standby state and clears an internal register, a flag register, a timer and a counter 52. CPU 34 then reads a program for executing steps 54 through 86 of a floppy 50 from a floppy disk unit 49 and writes the program to RAM 37 53. The control operation continues to be executed in accordance with a program of RAM 37 till the power supply is turned OFF.

Figure 10A:
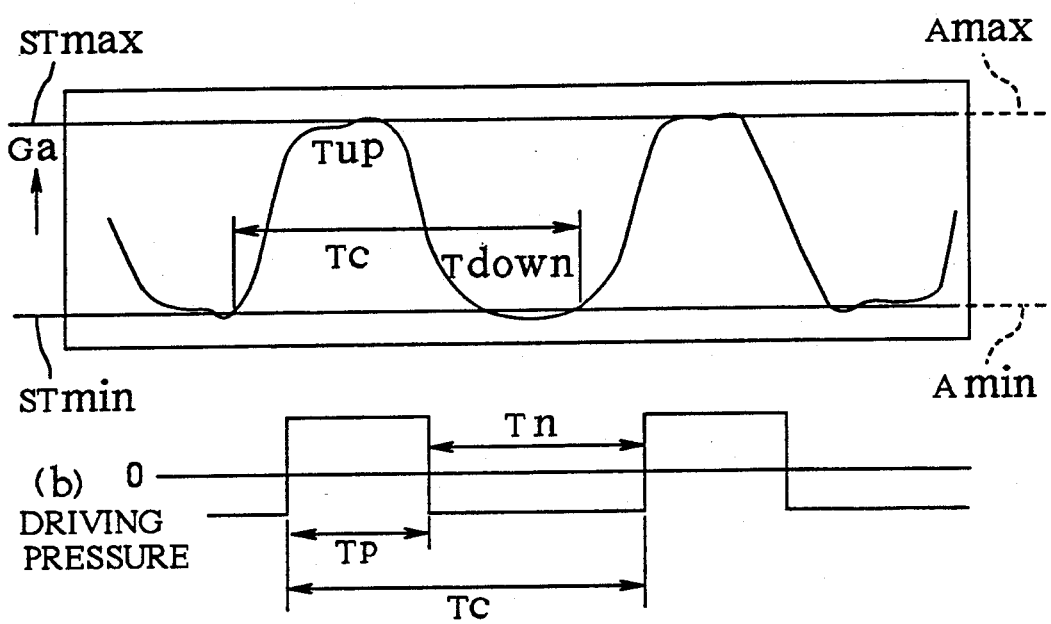
FIGS. 10a through 10d are graphic charts each showing a transition of the stroke Y of the passage 4.
Figure 10B:
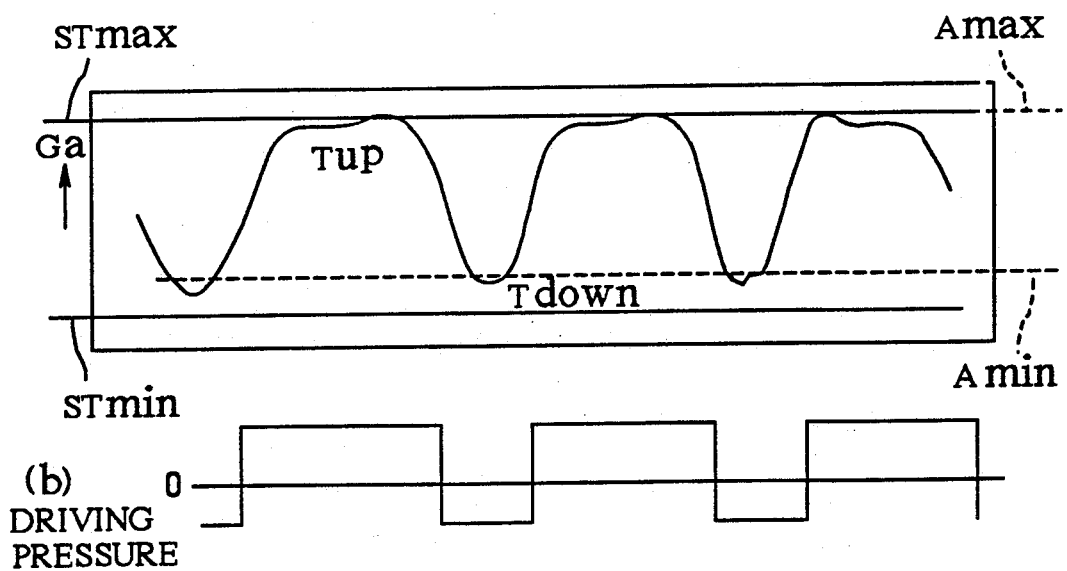
Figure 10C:
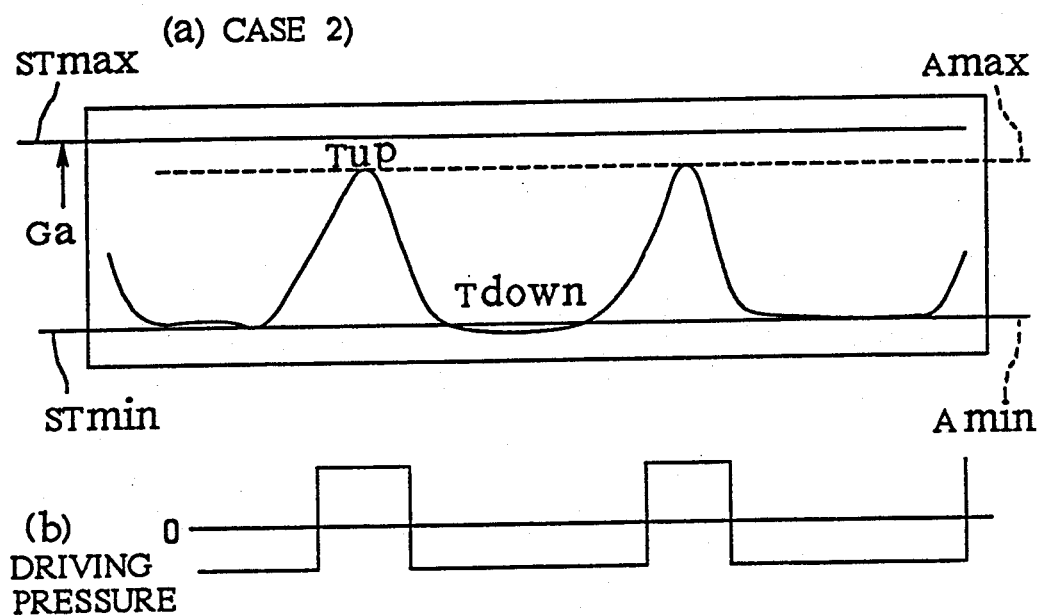
Figure 10D:
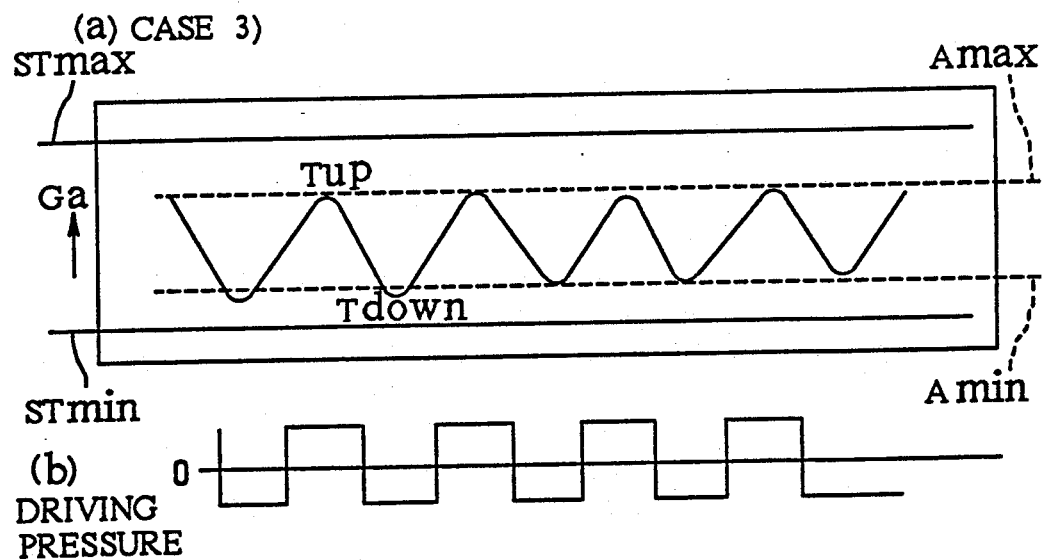
Figure 11A:
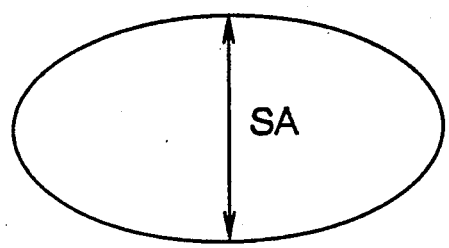
FIG. 11a is a plan view illustrating an image of the passage 4 and a top dead center value SA used for monitoring a low flow rate abnormality.
Figure 11B:
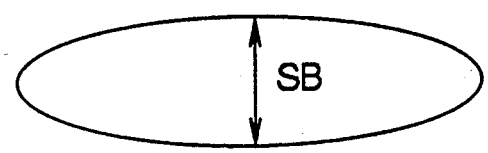
FIG. 11b is a plan vie willustrating an image of the passage 4 and a bottom dead center SB used for monitoring the low flow rate adnormality.
Figure 11C:
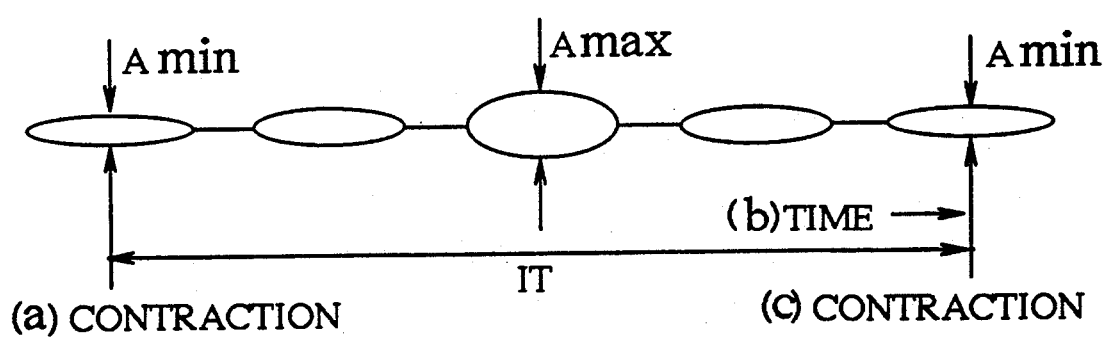
FIG. 11c is a plan view illustrating an image which varies in time series and a contraction cycle allowable maximum value IT.
Figure 12A:
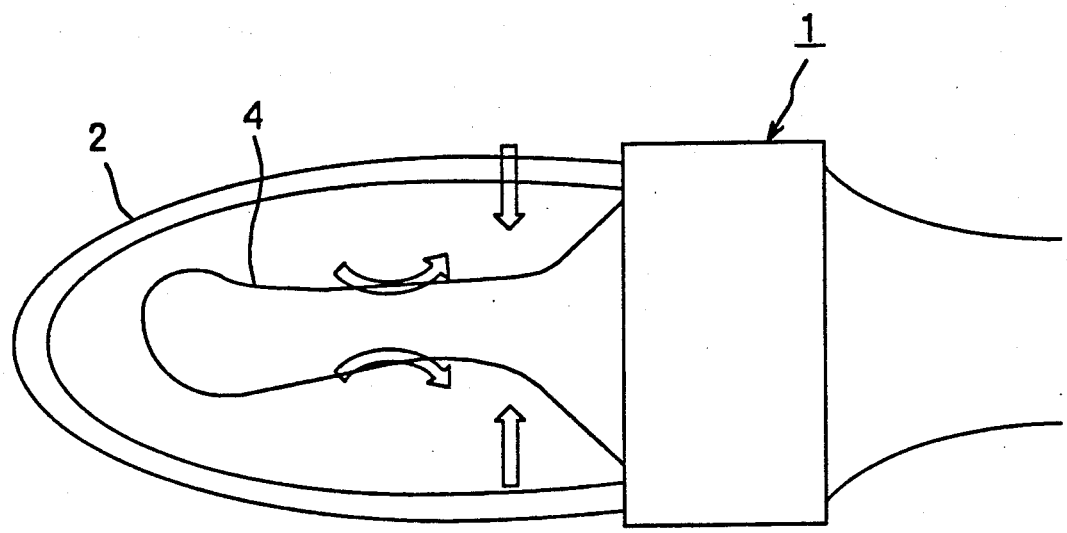
FIG. 12a is a vertical sectional view of an artificial heart 1, showing a contraction abnormal state of the passage 4.
Figure 12B:
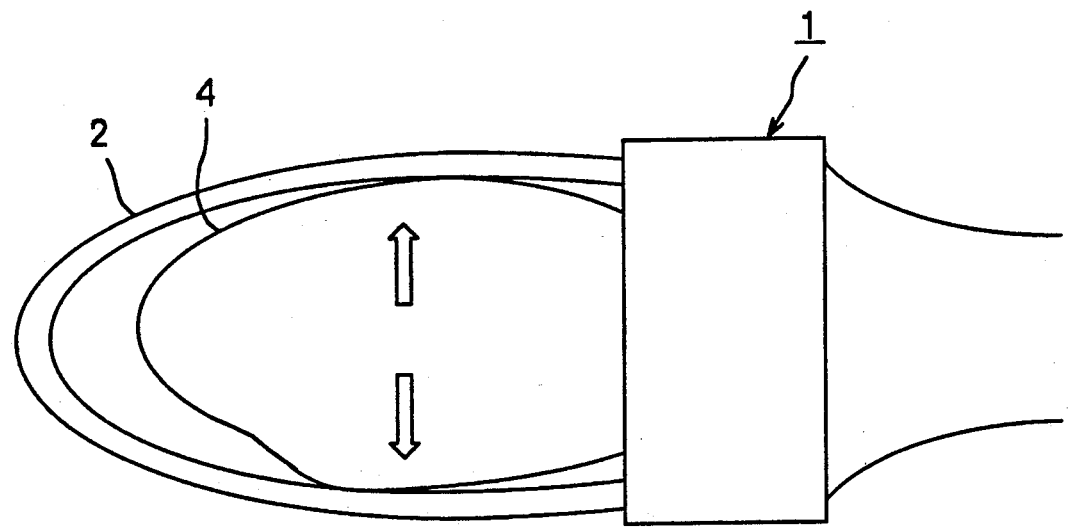
FIG. 12b is a vertical sectional view of the artificial heart 1, showing an expansion abnormal state of the passage 4.

To start with, CRT 53 displays a menu picture an input picture for promoting an operator's input, and inputs of the keyboard 41 are then read 54. Inputting is effected in the sequence of the synchronous/asychronouos modes, Tc a beat cycle, Yp a discharge period, SA (a top dead center stroke value for monitoring a low flow rate abnormality in the passage 4: FIG. 11a, SB (a bottom dead center stroke value for monitoring the low flow rate abnormality in the passage 4: FIG. 11b), IT (a contraction cycle allowable maximum value: FIG. 11c), STmax (an expansion peak set value of the passage 4: FIGS. 10a to 10d), STmin (a contraction peak set value of the passage 4: FIGS. 10a to 10d), Smax (an expansion limit value of the passage 4: FIG. 12b), Smin (a contraction limit value of the passage 4: FIG. 12a). Vol=f(Y) (a functional parameter for prescribing a relationship of a volume Vol which corresponds to a passage 4 width Y=Y2−Y1), and centroidal position. These items are displayed on the menu picture. The cursor at first indicates the synchronous/asychronous modes, this selected information being inputted by the operator by use of the keyboard 41. The synchronous or asynchronous mode, which has thus been selected, is indicated in an input field, and the cursor moves to the next SB position. The sequential inputting processes are effected in the above-described order. The inputting operation is ended up with Vol=f(Y), at which time CPU 34, while displaying the input information, gives an instructive indication saying If the conditions displayed are valid, execute a start input once. If there is a part to be corrected, move the cursor to this part and effect inputting once again. Upon the start input, CPU 34 gives the synchronous/asychronous modes, Tc the beat cycle and Tp the discharge period to the pumping controller 11 of the artificial heart driving module 10, thus giving an instruction of start. As a result, the artificial heart 1 starts working the passage 4 initiates repetitive contracting and expanding motions alternately at a cycle Tc and a discharge duty given by Tp/Tc×100%. After starting a drive of the artificial heart 1, CPU 34 issues an image take-in instruction (S1) to the image processing computer 17, which in turn gives an instruction to transfer a binary image signal to DMA 32 of the computer 17 at at timing when the computer 17 writes the binary image signal to A of the memory 23. This is then written to RAM 3 of the memory 42 and is additionally displayed on the menu picture. The transmission of the image take-in instruction S1 is repeated at a predetermined cycle, and an instructive indication saying Input the centroidal position of the suck, is added onto the menu picture while updating the display of the passage image. In the case of inputting the positional data by use of the keyboard 41, a mark (+) is attached to a position specified by the positional data on the display picture of the suck image. Subsequently, CPU 34 gives an indication dictating. If the conditions displayed are valid, execute a start input once. If there is a part to be corrected, move the cursor to this part and effect inputting once again. Immediately when start inputting is performed, CPU 34 transmits the image take-in signal S1 to the image processing computer 17 and gives an instruction to set a binary-coded threshold value 56. After the computer 17 has finished setting the binary-coded threshold value and transmitted a sign of "Ready", CPU 34 permits an internal timer interruption for transmitting image take-in signals S2 at a cycle defined such as to=1/30 sec 59. CPU 34 starts an internal timer to 60 and the clears registers n, k and j for storing data used for judging abnormalities of the passage 4 (A1). Subsequent to this step, CPU 34 starts timers B and D (A2, D1) and permits a receiving interruption for receiving and taking in transmission data Y1, Y2 and S from the computer 17. Then, a subroutine of centroid monitoring 65 is executed. After finishing the execution once, a step of input reading 66 is effected. When an input is given from the keyboard 41, a process corresponding to this input is performed 68. When a stop input is imparted from the keyboard 41, the process is returned to the step 54, where the display on the menu picture resumes. An instruction for stopping is given to the pumping controller 11. When receiving an input to modify the set data, the process moves back to the step 54, where displaying on the menu picture is effected. After starting a drive of the pump, on the occasion of modifications of the synchronous/asynchronous modes, Tc, Tp, SA, SB, IT, STmax, STmin, Vol=f(Y), Smax, Smin and centroidal position while the pump continues to be driven, the operator inputs modification by use of the keyboard 41. In response to this input, CPU 34 reads modification at a step of keyboard input reading 66, and the operation moves forward to a subroutine 54, where the menu picture is displayed. The operator adjusts the cursor to a modifying field on the menu picture and inputs modifying information.

Provided that no input is given from the keyboard in the subroutine 66, the operation advances to centroid monitoring 65.

Figure 3A:
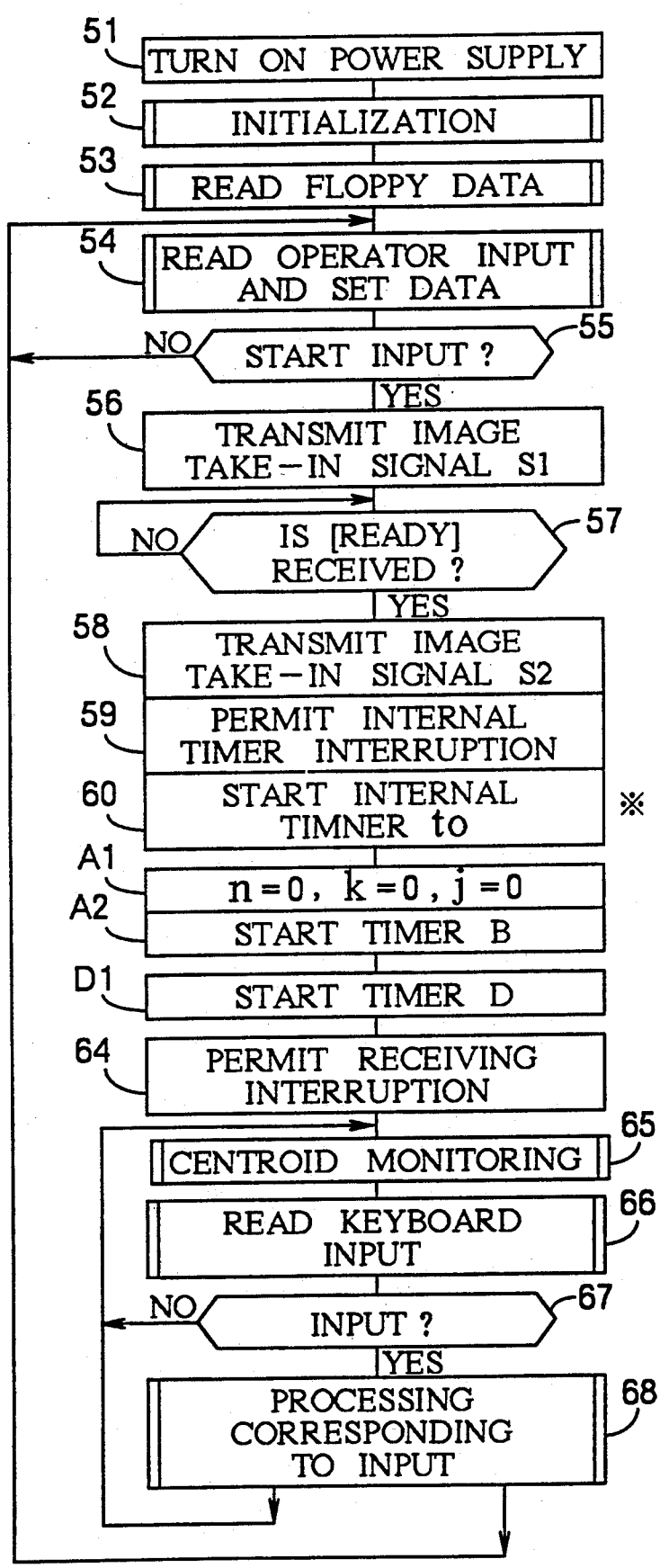

Referring to FIG. 3b, contents of internal timer interrupton 70 will be explained. If time-over of the timer to occurs, CPU 34 moves to internal timer interruption 70, where the image take-in signal S2 is transmitted to the computer 17 (71). The internal timer restarts (72), and then the operation returns to the process just before advancing to internal timer interruption 70 of the main routine (FIG. 3a).

As a result of executing internal timer interruption 70, the image take-in signals S2 are transmitted to the computer 17 at a cycle defined such as to=1/30 sec.

The computer 17, as will be mentioned later, reads the image data (gradation data) for one frame of the CCD camera 16 at that time in response to the signals S2 and writes the image data to the memory 24. Subsequently, the image data for one frame are binary-coded with binary-coded threshold values to obtain binary-coded image signals which are written to A of the memory 23. Based on the image signals of A, an upper fringe position Y1, a lower fringe position Y2 and an image area S (indicated by oblique lines of FIG. 9a) of an image of the suck 4 are computed. Pieces of data Y1, Y2 and S are sent to the computer 33. Hence, the data Y1, Y2 and S are tranferred from the computer 17 to the computer 33 virtually at the cycle to.

CPU 34 of the data processing computer 33, when the computer 17 transfer the data Y1, Y2 and S thereto, executes receiving interruption (80) shown in FIG. 3c. More specifically, CPU 34 receives and takes in the data Y1, Y2 and S (81) and then calculates a stroke width Y of the passage 4, which is given by Y=Y2−Y1 (82). CPU 34 executes stopping time monitoring (83), stroke deflection monitoring (84), overpressure monitoring (85) and feeding flow rate monitoring (86) in this sequence. Subsequently, the operation returns to the process just before moving on to receiving interruption (80) of the main routine (FIG. 3a). Since the data Y1, Y2 and S are sent from the computer 17 to the computer 33 virtually at the cycle to, the subroutines (83 through 86) thereof are executed virtually at the cycle to.

There will hereinafter be explained the contents of stopping time monitoring (83), stroke deflection monitoring (84), overpressure monitoring (85), feeding flow rate monitoring (86) and centroid monitoring (65) shown in FIGS. 3a with reference to FIGS. 4a to 8.

Turning next to FIGS. 2a through 2c, the description will deal with control processes executed by CPUs 18 and 19 of the image processsing computer 17. When making a current of the power supply (1), CPU 18 sets an I/O port at a signal level when being in standby state and clears an internal register, a flag register, a timer and a counter (2). CPU 18 waits for the image take-in signals S1 coming from the data process computer 33. Upon an arrival of the signals S1, and A/D converter 26 converts video signals for one frame which are transmitted from the CCD camera 9 into image data (gradation data) (4), and the thus converted image data are written to the memory 24 (5). A binary-coded threshold value of the image data is then set (6).

The step (6) of setting the binary-coded threshold value begins with creating a histogram, i.e., calculating a sum of densities of image data (density data) per dot with respect to every column in connection with the image data for one frame (256×256 pixels) of the CCD camera. A column in which the maximum value of the sum of densities is exhibited is judged, and there is computed a threshold value with which one-fourth of 256 pixels of that column become black (the passage portion). In the wake of this process, the video signals of the CCD camera are read per frame and at the same moment binary-coded to obtain binary-coded data from which an area S (the number of black pixels) of the black region is calculated. A maximum value Sm of the area S is detected. Upon a detection of this value, the video signals are likewise read per frame and binary-coded for computing the area S. A calculated area is equalized virtually to the maximum value Sm, in which case the video signals cease to be read. Written to the memory at this time are the image data (gradation data) when the passage 4 expands most (top dead center). Now, CPU 18 reduces the threshold value if the area Si is large. Whereas if small, the threshold value is increased. The image data of the memory 24 are binary-coded to compute an area Sj thereof. The area Sj is then compared with a standard value Ss with the intention of detecting a threshold value with which the area S1 becomes virtually equal to the standard value Ss. The thus detected value is set as a threshold value L. Upon a completion of setting this value L. CPU 18 transmits [Ready] to the data processing computer 33.

On receiving [Ready], CPU 34 of the data processing computer 33, as stated earlier, transmits the image take-in signal S2 to the image processing computer 17 at the cycle to.

Figures 9A, 9B:
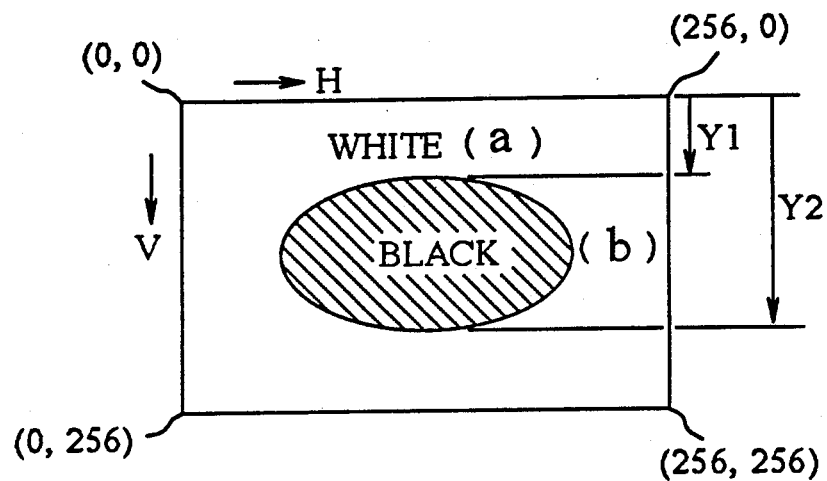
FIG. 9a is a plan view expessing images of a passage 4 in the form of binary values which are photographed by means of a CCD camera 16.
FIG. 9b is a plan view illustrating a one-dimensional array A of data representing a stroke Y of a passage 4 which is formed by CPU34, a one-dimensional array B of differential data thereof and a one-dimensional array C of data representing a stopping time T of the passage 4.

When receiving the image take-in signals S2 (7), CPU 18 of the image processing computer 17 converts the one-frame video signals of the CCD camera 9 into the image data (gradation data) by means of an A/D converter 26 and writes the thus converted image data to the memory 24 (8). The image data (one frame) of the memory 24 are binary-coded with a threshold value L preparatory to conversion into binary image signals in which 1 bit (1: black, 0: white) is provided per pixel; and the converted binary image signals are written to A of the memory 23 (9, 10). The thus written binary image signals, as illustrated in, e.g., FIG. 9a, represent a passage image (oblique lines: black) on the frame picture.

Next, CPU 18 accesses the binary image signals of the memory 23 column by column from upper and lower ends of the frame toward the center in a horizontal direction (an arrowed direction H). The columns in which a ratio of white pixels in one column to black pixels is 1:4 or greater are defined in association with an upper end Y1 and a lower end Y2 respectively (the upper and lower fringes of the passage image) (11 to 33: FIG. 9a). The area S (a sum of the black pixels) of the passage image is calculated (34 to 43). Subsequent to this step, the upper fringe data Y1, the lower fringe data Y2 and the area data S of the passage image are transferred to the data processing computer 33 (44).

The above-described processes (8 to 44) are performed each time the signal S2 is transmitted, and hence the data Y1, Y2 and S are transferred to the data processing computer 33 virtually at a cycle given by to =1/30 sec.

CPU 34 of the data processing computer 33, each time it receives the data Y1, Y2 and S, executes [receiving interruption] (80) shown in FIG. 3c, wherein firstly a width Y of the passage image in a vertical direction (V) is calculated such as Y=Y2−Y1; and secondly stopping time monitoring is executed (83).

Figure 4A:
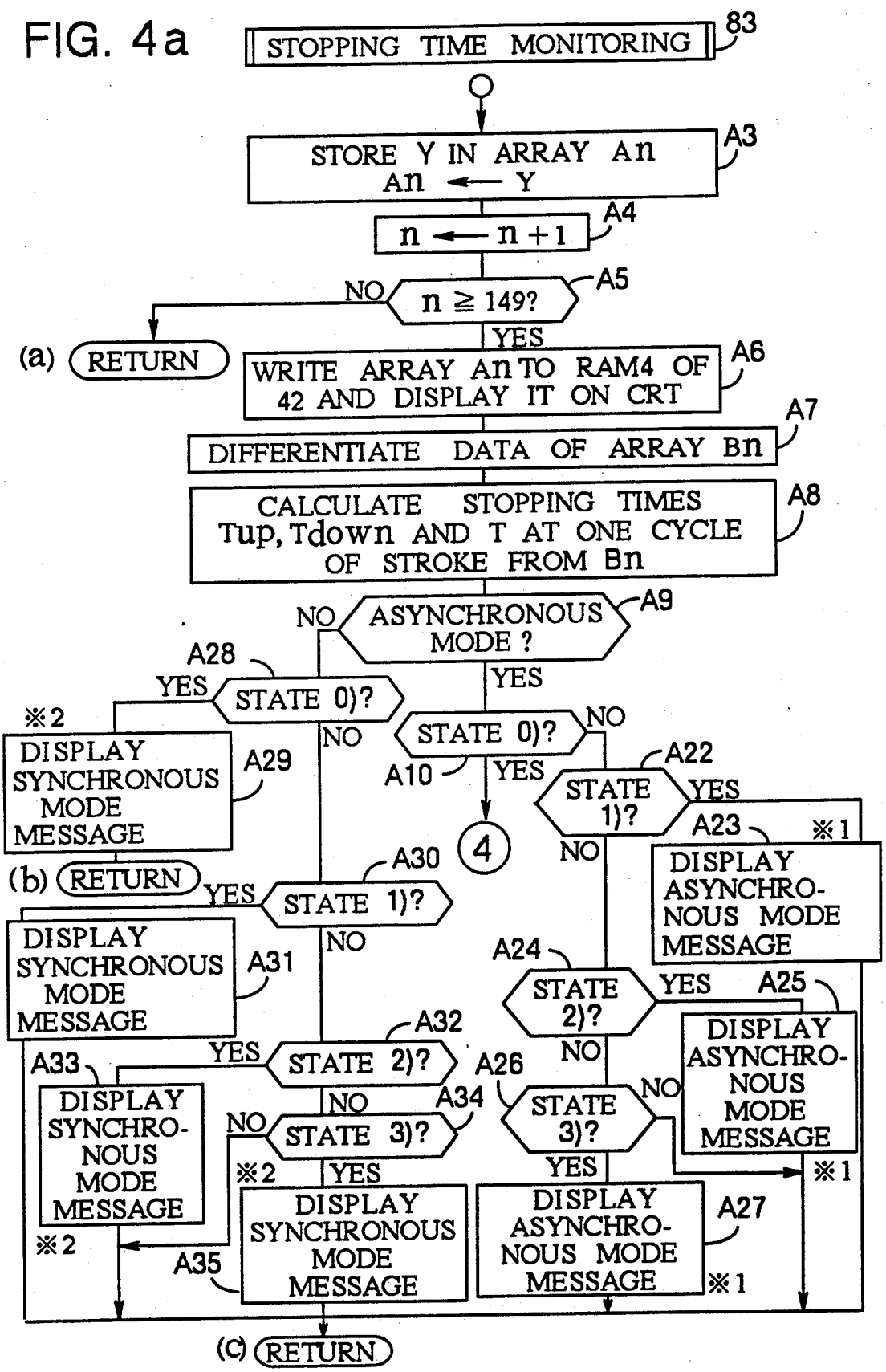
Figure 4B:
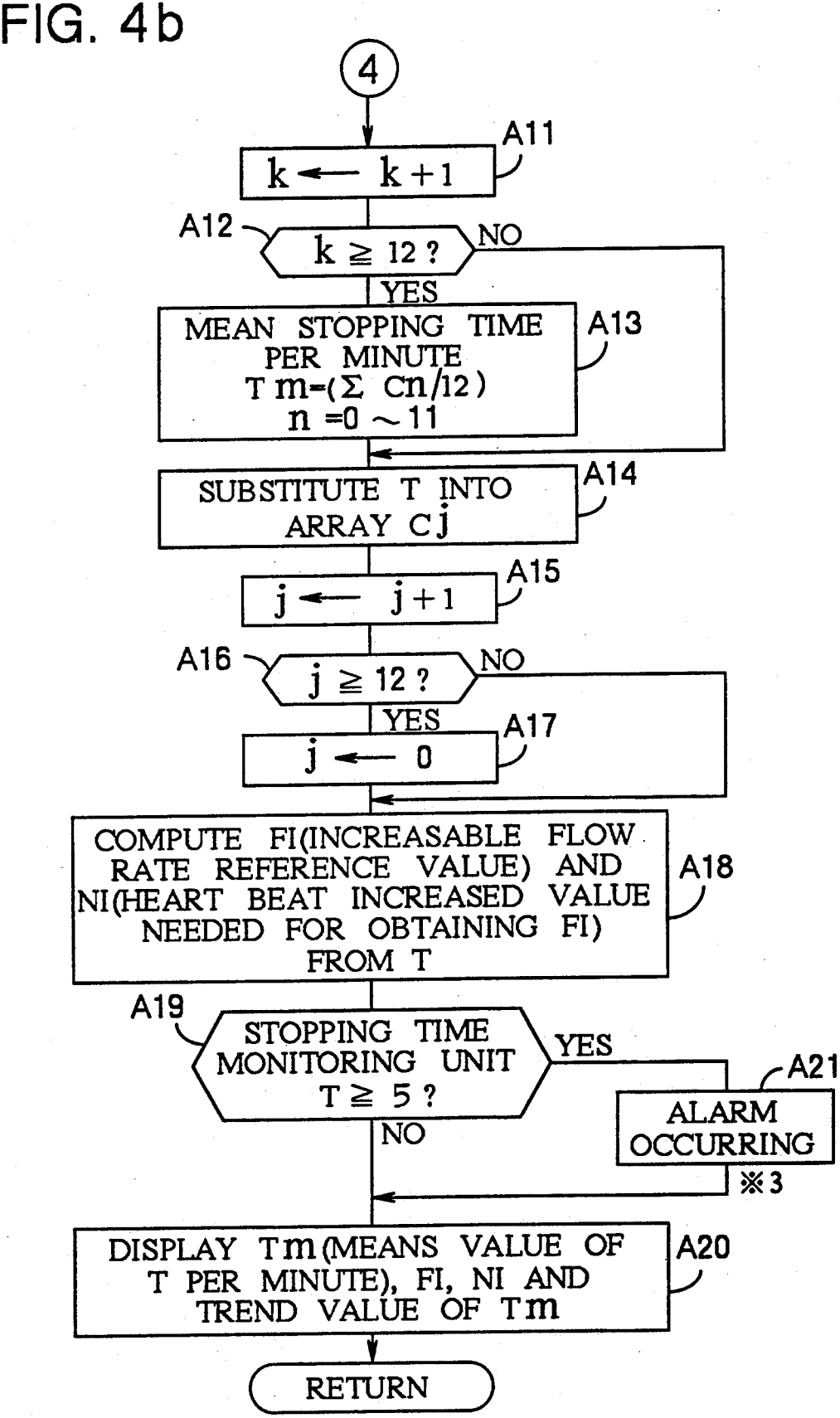

Turning to FIGS. 4a and 4b, there are shown contents of stopping time monitoring (83), wherein stroke data Y for 5 sec (30×5=150 pieces) which vary with a passage of time are so stored in the internal memory as to be arranged in a one-dimensional array A illustrated in FIG. 9b (A3 to A5). Subsequently, the data of the one-dimensional array A are subjected to linear differential arithmetic operations on a unit of to =1/30 sec, thereby obtaining 149 pieces of differential values. These values are stored in a one-dimensional array B (A6, A7). Based on the data of the one-dimensional arrays A and B, the stroke Y and the differential values are expressed as Ga and Gb respectively in a graphic chart of FIG. 9c. A flat part of Ga (a part of 0 in Gb) indicates a period for which no variation can be seen in the stroke width. On the basis of this, a period for which 0 continues in Gb at a one-pulsating cycle is obtained as a stopping time T. The stopping times T for one minute (60/5=12 pieces) at the one-pulsating cycle are stored in a one-dimensional array C (FIG. 9b) with a view to obtaining a mean value of the values of the one-dimensional array C. Next, a mean one-pulsating cycle stopping time Tm for one minute is calculated. A maximum value Amax and a minimum value Amin of the strokes are picked out in Ga (FIG. 9c). Subsequently, there are computed a continuous time (a 0-period in Gb) of the maximum value Amax, i.e., a top dead center period Tup and a continuous time (a 0-period in Gb) of the minimum value Amin, viz., a bottom dead center period Tdown (A8).

One cycle of one beating of the artificial heart 1 is designated at Tc in FIG. 9c, while a period for which the action is effective in discharging the blood is expressed by Tc−(Tup−Tdown). As depicted in FIG. 9c, even if one cycle Tc of one beating of the artificial heart 1 is reduced by a period which is twice the shorter of the periods Tup and Tdown, the stroke width given by (Amax−Amin) does not change. Hence, in the asynchronous mode (of arbitrarily setting the pulsating cycle by means of the artificial heart driving module 10), it is possible to reduce the one pulsating cycle Tc of the artificial heart 1 without changing a one-beating quantity.

Let F be a blood flow rate of one beating at a beat number N per minute, let Tc be a one pulsating cycle, let Tup and Tdown be stopping periods at the top and bottom dead centers respectively, and let Tsmall be the smaller of the stopping periods Tu and Tdown. An effective acting time Tg for one minute is given by:

$$Tg = N \times [Tc - (Tup + Tdown)]$$

An ineffective time Tb is expressed such as:

$$Tb = N \times (Tup + Tdown)$$

A one pulsating cycle TcD reduced with no variation in the beating quantity is given by:

$$TcD = Tc - 2Tsmall$$

A flow rate Fm at which the blood can be pulsed out per minute at the one-pulsating cycle Tc is given such as:

$$Fm = N \times F$$

A flow rate FmD at which the blood can be pulsed out per minute at the one-pulsating cycle TcD is given by:

$$FmD = (60/TcD) \times F$$

$$N \times Tc = 60,$$

and $$Tb + Tg = 60$$

Hence, $$FmD = (N \times Tc/TcD)$$

A flow rate FI (one minute) increased due to a reduction of the one-pulsating cycle from Tc down to TcD is expressed such as:

$$\begin{aligned} FI &= FmD - Fm \\ &= (N \times Tc/TcD) \times F - N \times F \\ &= F[N \times (Tc - TcD)]/TcD \\ &= 2F \cdot N \cdot Tsmall/TcD \end{aligned}$$

A heartbeat number Nd per minute for obtaining the one-pulsating cycle TcD is given by:

$$Nd = 60/TcD$$

N.Tc=60, and TcD=Tc−2Tsmall, so that a heartbeat increasing number NI per minute for obtaining the one-pulsating cycle TcD is expressed by:

$$\begin{aligned} NI &= Nd - N \\ &= 60/TcD - N \\ &= N \cdot Tc/TcD - N \\ &= N \cdot (Tc - TcD)/TcD \\ &= 2N \cdot Tsmall/TcD \end{aligned}$$

An effective driving time per beat is (Tc−Tup−Tdown), and TcD=Tc−2Tsmall. Therefore, an ineffective time Tbd at the heart beat number Nd is given by:

$$\begin{aligned} Tbd &= Nd \times (TcD - (Tc - Tup - Tdown)] \\ &= Nd \times (Tup + Tdown - 2Tsmall) \end{aligned}$$

The explanation given above has dealt with a case (FIG. 10a) where the artificial heart 1 is at full-strokes, and there are dormant periods both in an upper stroke limit and in a lower stroke limit. However, as illustrated in FIGS. 10b through 10d, there exists a possibility in which no dormant period of the upper or lower limit is provided, or alternatively no full-stroke is effected both in the upper limit and in the lower limit. Under such circumstances, the flow rate of the artificial heart 1 drops, and in addition, the stroke width is diminished, thereby increasing a possibility of causing the thrombus.

Now, the above-described operating states of the artificial heart 1 will be classified into the following four cases, where Amax is the value of Y=Y2−Y1 (upper peak: top dead center) when a photographed image of the suck 4 of the artificial heart 1 expands at the maximum, Amin is the value of Y=Y2−Y1 (lower peak: bottom dead center) when the photographed image of the passage 4 thereof contacts at the minimum, STmax is the upper limit set value, STmin is the lower limit set value, Tup is the upper peak dormant period, and Tdown is the lower peak dormant period.

Case 0): FIG. 10a
   Amin=STmin, Tdown>0,
   Amax=STmax, Tup>0
Case 1): FIG. 10b
   Amin>STmin, Tdown=0,
   Amax=STmax, Tup>0
Case 2): FIG. 10c
   Amin=STmin, Tdown>0,
   Amax<STmax, Tup=0
Case 3): FIG. 10d
   Amin>STmin, Tdown=0,
   Amax<STmax, Tup>0

CPU 34 functions to calculate the values Tup, Tdown and T in a step A8. Considering these values, among the foregoing cases 0) through 3) CPU 34 judges a case of the driving state of the artificial heart 1. When being in the asynchronous mode in the case 0), the flow rate FI and the heartbeat increasing number NI are calculated (A10 to A18). Whether the dormant period T of one-pulsating cycle is more than 5 sec or not is checked (A19). If greater than 5 sec, this implies an operational abnormality. Immediately, a buzzer 51 is energized to display the abnormality caused (the dormant period is excessively long) in a filed (*3) of [ALARM] of a display region DA1 (FIG. 14a) of CRT 53 (A19, A21). More specifically, abnormality informing data displayed in the field (*3) of [ALARM] is written to RAM 1 of a memory 42 for storing display data in the display region DA1 and is then displayed on CRT 53. After completely checking the abnormality in the dormant period T, CPU 18 writes T, Tup, Tdown, FI and NI together with Tm to RAM 1 of the memory 42 for storing the display data in the display region DA1 on a picture 53 (FIG. 14a) of CRT 53. Those values are indicated in the display region DA1 (A20). Only the storage of data Y is performed till T, Tup, Tdown, FI and NI are calculated (A3 through A8) after storing the data Y for 150 times in the one-dimensional array A (FIG. 9b and subsequently the data Y for 150 times are stored. Hence, the values T, Tup, Tdown, FI and Ni are updated for every 5 sec (150×1/30 sec, 1/30 sec=To). The mean one-pulsating cycle stopping time Tm is calculated each time the values T, Tup, Tdown, FI and Ni are computed 12 times, and it follows that Tm is updated per minute. A predetermined number of the values Tm (for several hours) are held, and trend values thereof are displayed in the display region DA1.

When being in the asynchronous mode in the case 0), as discussed above, with respect to the driving pressure a duty ratio of a positive pressure to a negative pressure is modified such as Tdown=Tup, with the result that Tbd reaches the minimum; and the conditions can also be changed to exhibit the maximum flow rate. When being in the asynchronous mode in the case 0), however, Tup, Tdown, T, FI, NI, Tm and the trend of Tm are displayed in the display region DA1. The operator therefore, while looking at the items indicated in the display region DA1 (FIG. 4a) of CRT 53, recognizes that there are still an allowance for the driving states in the case of Tm (a mean value per minute of the dormant period T during one pulsation) being large and a possibility to increase the flow rate by FI (an increasable flow rate reference value) by referring to Tm, FI and NI (a heartbeat increasing value required for obtaining FI). From the heartbeat increasing value NI the operator is able to further know a degree to which the number of heartbeats is required to increase. It is therefore feasible to handle the condition under which the artificial heart 1 is driven in an optimal driving state. Namely, the parameters (Tc, Tp: FIG. 10a) of the driving conditions are modified (adjusted) by use of the keyboard 41. If the dormant period T during one pulsation comes to 5 sec or greater, the buzzer 51 sounds, and simultaneously an alarm message is displayed in the field (*3) of [ALARM] of the display region DA1. The buzzer 51 arouses an attention of the operator which in turn can recognize a content of abnormality from the field of [ALARM] of the display region DA1 of CRT 53.

When the case 1) is judged in the asynchronous mode, CPU 34 modifies the contents of the display region DA1 to those shown in FIG. 4b, and displays a message saying [Shortage of the lower limit stroke. Change the driving pressure duty ratio of Tp/Tc to establish a relationship of Tdown=Tup] in a message filed (*1). In the case 1), since the lower limit stroke is not yet reached, there is a probability that the stroke width is small while the flow rate is insufficient. At this time, the duty ratio (Tp/Tc×100%: FIG. 10a) of a positive pressure to a negative pressure in association with the driving pressure is handled so that the relationship of Tdown=Tup becomes valid (in this case, the lower limit stroke is insufficient, and hence Tp is decreased with no variation in Tc), the driving state shifts to the case 0) or 3), thereby imparting, as described above, a message.

When the case 2) is judged in the asynchronous mode, CPU 34 modifies the contents of the display region DA1 to those shown in FIG. 4b, and indicates a message saying [Shortage of the upper limit stroke. Modify a duty ratio of Tp/Tc associated with the driving pressure to establish Tdown=Tup] in the message filed (*1). In the case 2), since the upper limit stroke is not yet reached, and there is a probability that the stroke width is small while the flow rate is insufficient. At this time, the duty ratio (Tp/Tc×100%: FIG. 10a) of a positive pressure to a negative pressure in association with the driving pressure is handled so that the relationship of Tdown=Tup becomes valid (in this case, the upper limit stroke is insufficient, and hence Tp is increased with no variation in Tc), the driving state shifts to the case 0) or 3), thereby imparting, as described above, a message.

When the case 3) is judged in the asynchronous mode, CPU 34 modifies the contents of the display region DA1 to those shown in FIG. 4b, and indicates a message saying [Shortage of an absolute time for feeding out the blood. Reduce the heartbeat number N (increase Tc) to establish relationships of Tdown>0 and Tup>0, or increase a blood feed-out velocity by rising the driving pressure]. In the case 3), the absolute time for attaining a full-stroke within one cycle Tc lacks unlike the cases 0) to 2) wherein one cycle Tc includes the dormant period T. It is therefore required to increase the blood feed-out velocity by extending the time Tc of one cycle or augmenting the driving pressure. The extension of Tc implies an increase in the heartbeat number N. The valve Tup and/or Tdown exceeds 0 by extending Tc or increasing the driving pressure. The operating state comes into the cases 0) and 1) or 2) (the operations described above are A22 through A27).

In the synchronous mode wherein the artificial heart 1 is pulsated synchronizing with timings at which the heart of a living body beats, the heartbeat number N of the artificial heart 1 depends on the number of heartbeats of the living body. Hence, the heartbeat number can not be controlled. Namely, the heartbeat number N (Tc) is unmodifiable in the synchronous mode. Such being the case, Tdown=Tup is established by modifying a duty ratio of a positive pressure (Tp) to a negative pressure (Tc−Tp) in association with the driving pressure (by adjusting Tp in this embodiment) in the synchronous mode, thereby obtaining the maximum stroke at the heartbeat number determined by a status-in-quo driving pressure.

Figure 14A:
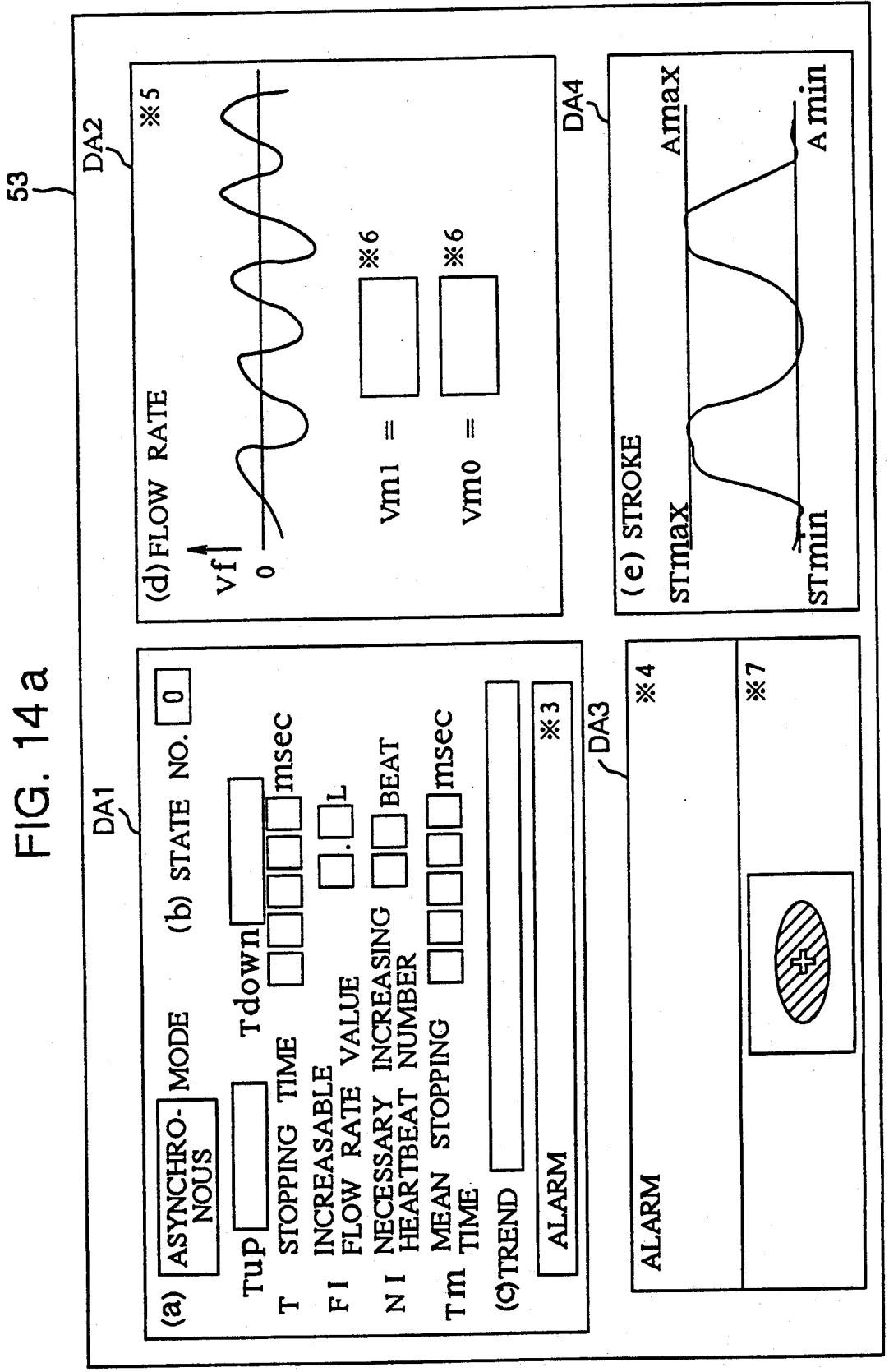
FIG. 14a is a plan view depicting a display picture of CRT 53 illustrated in FIG. 1.
Figure 14:
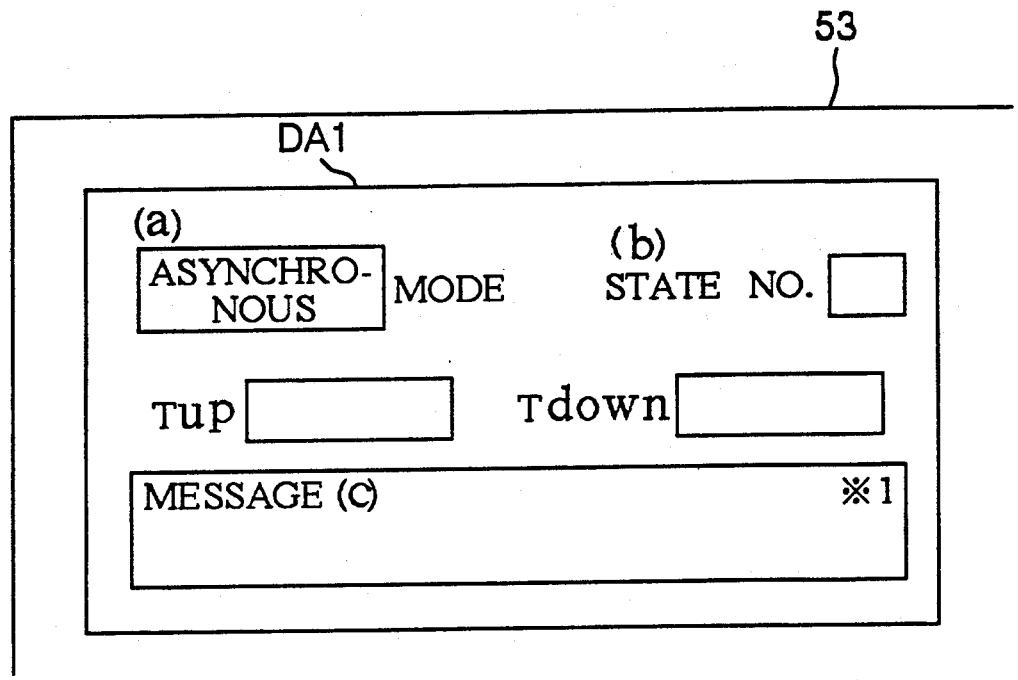
FIGS. 14b and 14c are plan views each partly showing the display picture of CRT 53 of FIG. 1.
Figure 14:
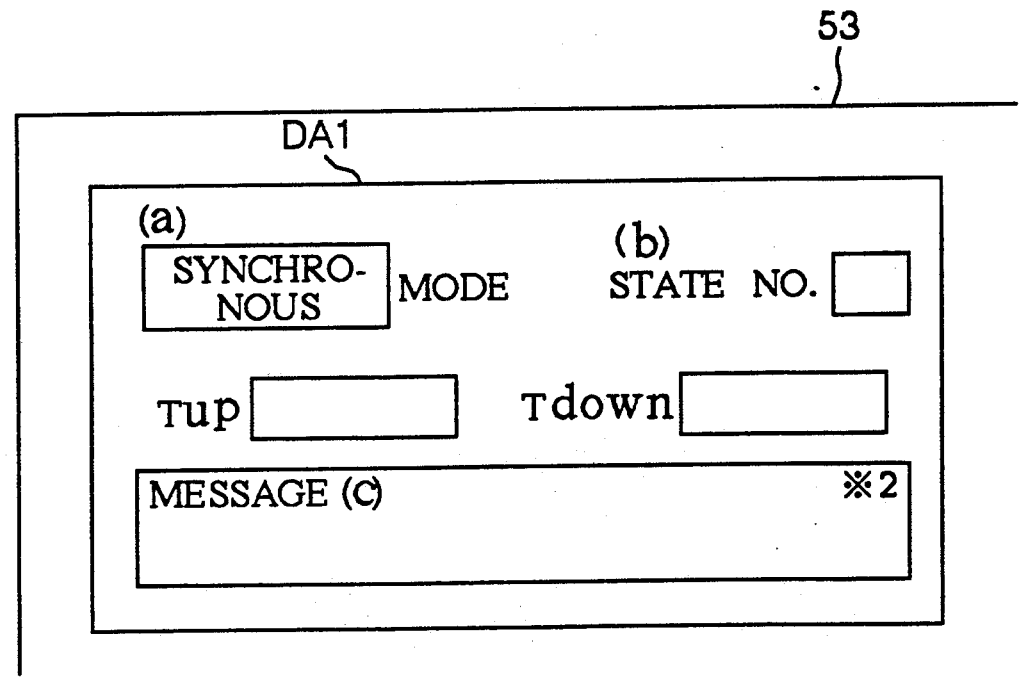

When being in the synchronous mode in the case 0), CPU 34 modifies the contents displayed in the display region DA1 to those shown in FIG. 14c and then indicates a message saying [As the mode is synchronous, the flow rate can not be increased even by changing the driving conditions. The flow rate is kept even by reducing the driving pressure] in a message filed (*2). When being in the synchronous mode in the case 1), a message of Shortage of the lower limit stroke. Modify a driving pressure duty ratio given by Tp/Tc to establish Tdown=Tup is indicated in the message filed (*2) of the display region DA1 of FIG. 14a. When being in the synchronous mode in the case 2), a message of [Shortage of the upper limit stroke. Modify a driving pressure ratio given by Tp/Tc to establish Tdown=Tup] is displayed in the message field (*2) of the display region DA1 of FIG. 14c. When being in the synchronous mode in the case 3), a message saying [Shortage of the absolute time for feeding out the blood. Reduce a driving pressure to establish Tdown>0 and Tup>0] is displayed in the message filed (*2) of the display region DA1 depicted in FIG. 14c.

A variety of the foregoing representations and messages are displayed corresponding to the operating states of the artificial heart 1 by effecting the process of stopping time monitoring (83) described above. The operator recognizes the operating state thereof by referring to the display DA1. The operator is capable of adjusting the operating state in which to bring about a desired flow rate of the blood to the greatest possible degree by inputting a modifications of the operating condition data through the keyboard 41.

Figure 5:
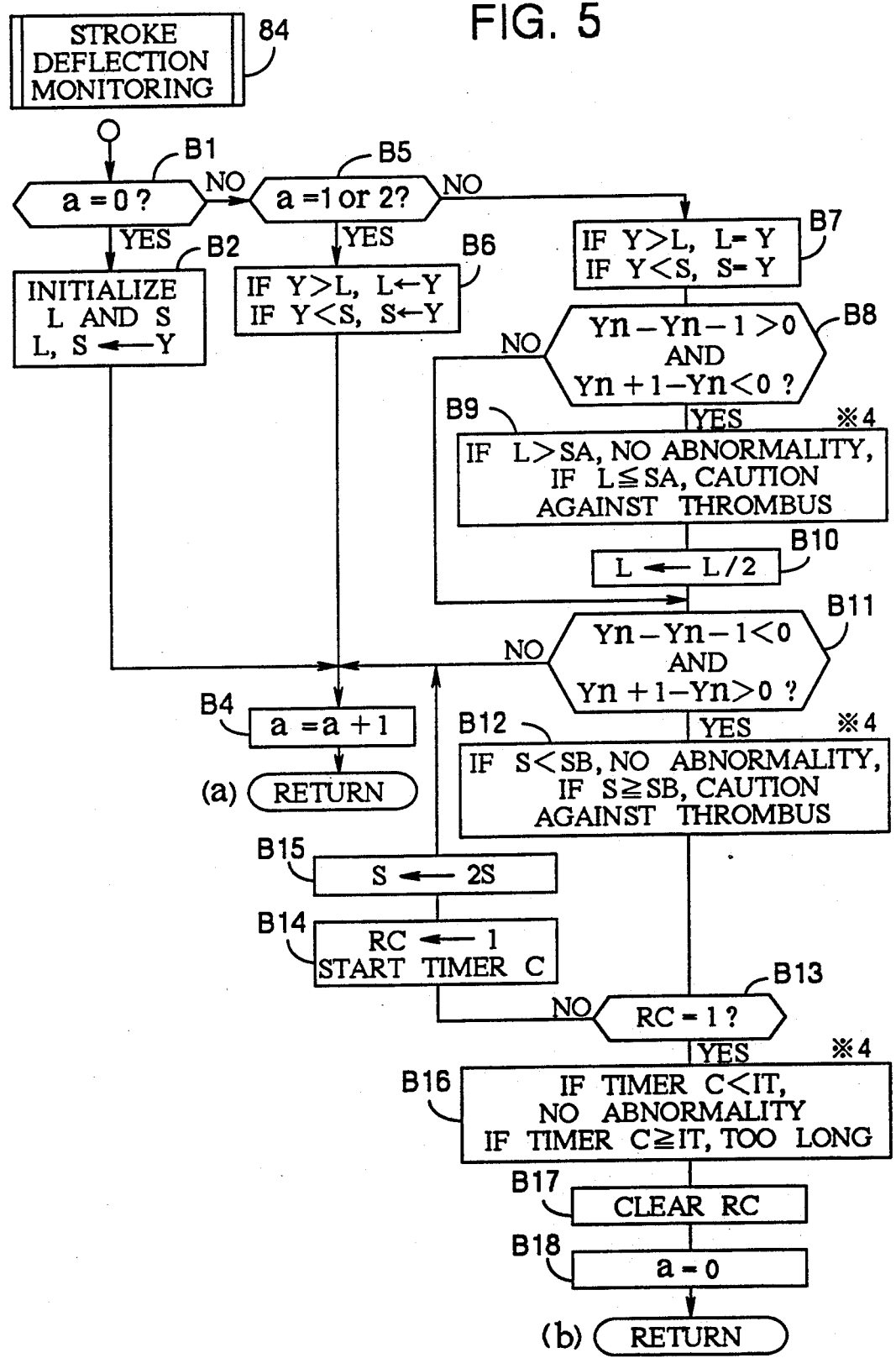

Contents of stroke deflection monitoring (84) will next be explained with reference to FIG. 5. Parts of the artificial heart 1, which come in contact with the blood, undergo an antithrombotic treatment, whereby the thrombus is hard to occur. Under normal using conditions, the blood flows at an adequate velocity. The blood does not stagnate in an blood pump as well as in the parts that contact the blood, and the platelets are not thereby activated. Hence, no thrombus is produced. If a flow rate of the artificial heart 1 is extremely small (a stroke Amax-Amin per beat is small; or alternatively, though the stroke is sufficient, an interval Tc from one beat to the subsequent beat is too long), the blood tends to be stagnant because of a long time for which the flowage stops when the blood runs at a low velocity. As a result, the blood stagnation is caused in the parts of the artificial heart 1 which contact the blood, thereby easily activating the platelets. This in turn facilitates the generating of thrombus; and there is also increased a risk in which the activated platelets are scattered over the respective portions of the living body to clog peripheral blood vessels. For this reason, there are set a minimum flow rate under which the amount of blood should not decrease, a least stroke and a maximum pulsation interval IT. If the stroke of the passage 4 deviates from a normal range and biases on an expanding or contracting side, the operating state of the suck varies, whereby the blood is apt to stagnate locally in the passage. Detecting the bias of stroke, when a normal stroke (e.g., STmax and STmin shown in FIG. 10a) is developed, involves a step of prescribing a set value SA (FIG. 11a) for detecting a stroke abnormality during the expansion and also a set value SB (FIG. 11b) for detecting a stroke abnormality during the contraction. The value Sa is smaller than STmax, while the value SB is greater than STmin, wherein SA>SB. These values SA and SB are inputted by the operator by use of the keyboard 41 in a step of reading an input by the operator and setting the data (54). When a stroke width Amax during the expansion of the passage 4 is less than the value SA, or when a stroke width Amin during the contraction thereof exceeds the value SB, the passage 4 biases on an excessive contraction side or an excessive expansion side. This implies that cautions about the thrombus are needed. If the pulsation interval Tc (for instance, as illustrated in FIG. 11c, an interval between a bottom dead center of one beat and that of the next beat) is in excess of IT, it follows that the cautions should be paid for the thrombus.

Initially, CPU 34 clears a register L for judging Amax and a register S for judging Amin and writes the stroke Y which has been calculated (the first time: a=0) in a step 82 (FIG. 3c) just before this clearing process. Subsequently, CPU 34 newly computes the stroke Y (the second and third times: a=1, 2) in the step 82. The computed stroke Y is compared with a content of the register L this time. If the stroke Y is larger than the content of the register L, the stroke Y is updated and written to the register L. Then, the stroke Y is compared with a content of the register S. If Y is smaller than the content of the register S, the stroke Y is updated and written thereto (B6). Thereafter, the calculated stroke Y undergoes a comparison with the content of the register L each time the stroke Y is newly calculated. When Y is greater than that of the register L, the stroke Y is updated and written thereto. The stroke Y is compared with the content of the register S. If Y is less than the content thereof, the stroke Y is updated and written to the register S (B7). $Y(Y_{n+1})$ obtained this time is compared with $Y(Y_n)$ computed last time and $Y(Y_{n-1})$ calculated at the before-last time. From these comparative results, there is made a judgment as to whether or not the passage changes from an expanding state to a contracting state, and vice versa (B8, B11). If a changeover from the expansion to the contraction is effected (at this time the top dead center data Amax exists in the register L), whether the data Amax of the register L exceeds the value SA or not is checked. If larger than SA, this implies a normal state. Whereas if smaller than SA, it is required that attention be paid for the thrombus. The buzzer 51 is then energized. A message saying [Be cautious about the thrombus. Increase the driving pressure or the duty (Tp) (elongate Tp)] is written to RAM 3 of the memory 42 for storing display data of a display region DA3 of CRT 53 and displayed in an [ALARM] filed (*4) of the display region DA3 (B9). A value that is one-half of the content at the time is updated and written to the register L (B10). If a changeover from the contraction to the expansion is performed (at this time the bottom dead center data Amin exists in the register S), whether the data Amin of the register S is less than the value SB or not is checked. If smaller than SB, this implies a normal state. Whereas if more than SB, it is needed that the attention be paid for the thrombus. The buzzer 51 is then energized. A message of [Be cautious about the thrombus. Decrease the duty (Tp) (shorten Tp)] is written to RAM 3 of the memory 42 for string the display data of the display region DA63 of CRT 53 and indicated in the [ALARM] field (*4) of the display region DA3 (B12). Subsequent to this step, a content of a flag register RC is checked (B13). If the content is 0 (a timer C for measuring time is not yet started), [1] indicating that the timer C is starting is written to a register RC. The timer C is started (B14), and a value that is twice the value thereof at this starting time is written to be register S (B15). If RC is 1 when performing the checking process in the step B13, since the timer C has already been started just when detecting the lower peak once, a time value of the timer C at this time represents a range from the lower peak shown last time to the upper peak indicated this time. The time value of the timer C is then compared with IT. If the time value is larger than IT, the buzzer 51 is energized. A message saying [Be cautious about the thrombus. Reduction in the pulsating cycle Tc is needed.] is written to RAM 3 of the memory 42 for storing the display data of the display region DA3 of CRT 53 and displayed in the [ALARM] field (a text information display field) (*4) of the display region DA3 (B16). Upon a completion of these processes, the timer C is cleared (B17), and subsequently a register a is cleared (B18).

As discussed above, the stroke operating mode of the passage 4 is monitored on the basis of the image of the passage 4. When a probability of causing the thrombus increases, the buzzer 51 automatically sounds. A notice indicating the necessity for paying attention to the thrombus and a countermeasure against it are displayed in the display region DA3 of CRT 53. The operator is allowed to modify the driving conditions of the artificial heart 1 via the keyboard 41, referring to these items displayed therein.

Figure 6:
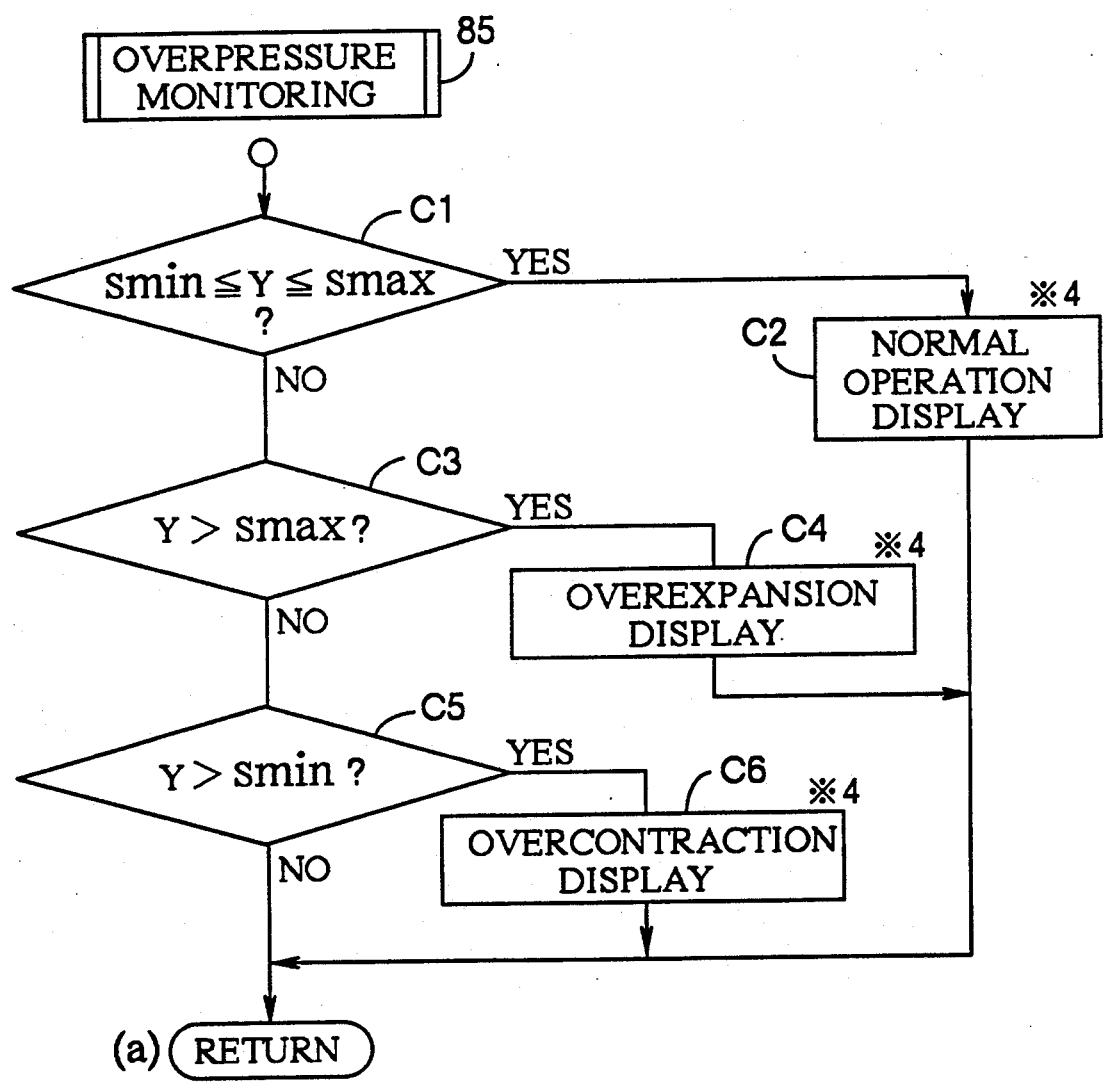

Next, a full detail of overpressure monitoring (85) will be explained with reference to FIG. 6. The artificial heart 1 has a rated range of the stroke width Y in terms of structure. If driven in excess of this range, the artificial heart 1 is to undergo structurally serious damages, with the result that the living body will probably be exposed to a remarkably dangerous situation. One cause may be an overcollapse, depicted in FIG. 12a, of the passage 4, and the other may be an overexpansion illustrated in FIG. 12b. The overcollapse acts to apply excessive stress on the passage 4, which in turn presents a problem pertaining to the mechanical durability thereof and increases the probability that the thrombus occurs due to the easy-to-activate platelets in association with an augment in rubbing action of the suck 4. Whereas in the case of overexpansion, an external surface of the passage 4 impinges and rubs on an inner wall surface of the internal casing 2, resulting in a drop in the mechanical durability of the passage 4.

The operator inputs the stroke Y calculated in the step 82 in accordance with the subroutine 54 by use of the keyboard 41, while CPU 34 reads this stroke Y and compares it with Smax (an expansion limit value of the passage 4) set in the internal register and Smin (a contraction limit value of the suck 4). If the stroke Y exceeds Smax, an overexpanding abnormality is indicated in the [ALARM] field (*4) of the display region DA3 of CRT 53. When being smaller than Smin, an excessive contraction abnormality is displayed therein. Simultaneously, the buzzer 51 is energized (C4, C6).

The overexpansion (FIG. 12b) and overcontraction (FIG. 12a) of the passage 4 are automatically detected in the manner described above, thereby informing the abnormalities. In response to this abnormality notification, the operator takes measures, i.e., makes adjustments and inspections of reducing the driving pressure, modifying the duty (changing Tp) and checking the abnormalities in the pump. If a failure can be seen in the artificial heart 1 itself, this artificial heart is replaced with new one. It is feasible to maintain the normal driving state of the artificial heart 1 linked to the living body in this manner and prevent a big accident such as a rupture of the passage 4.

Figure 7:
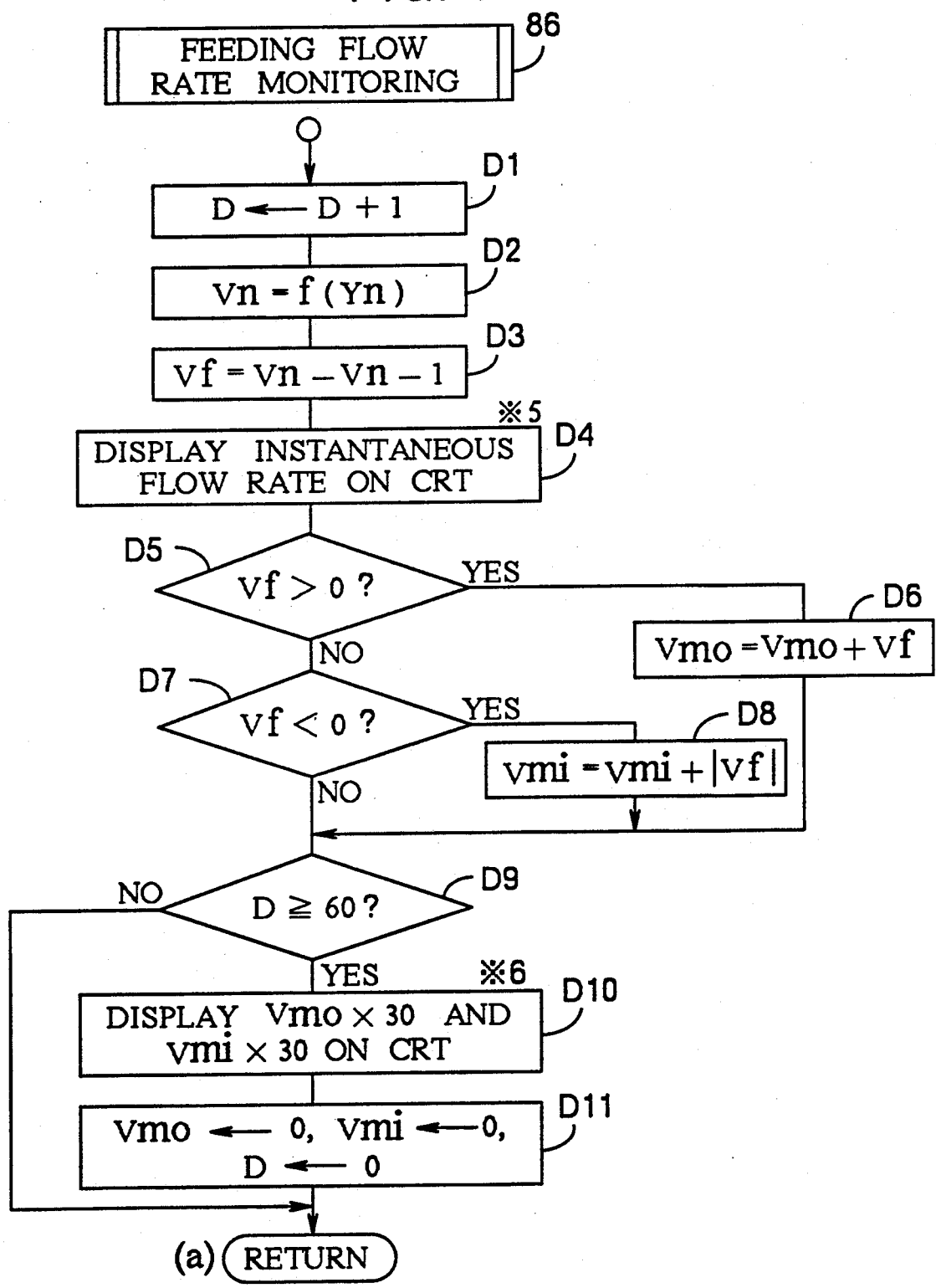
Figure 13:
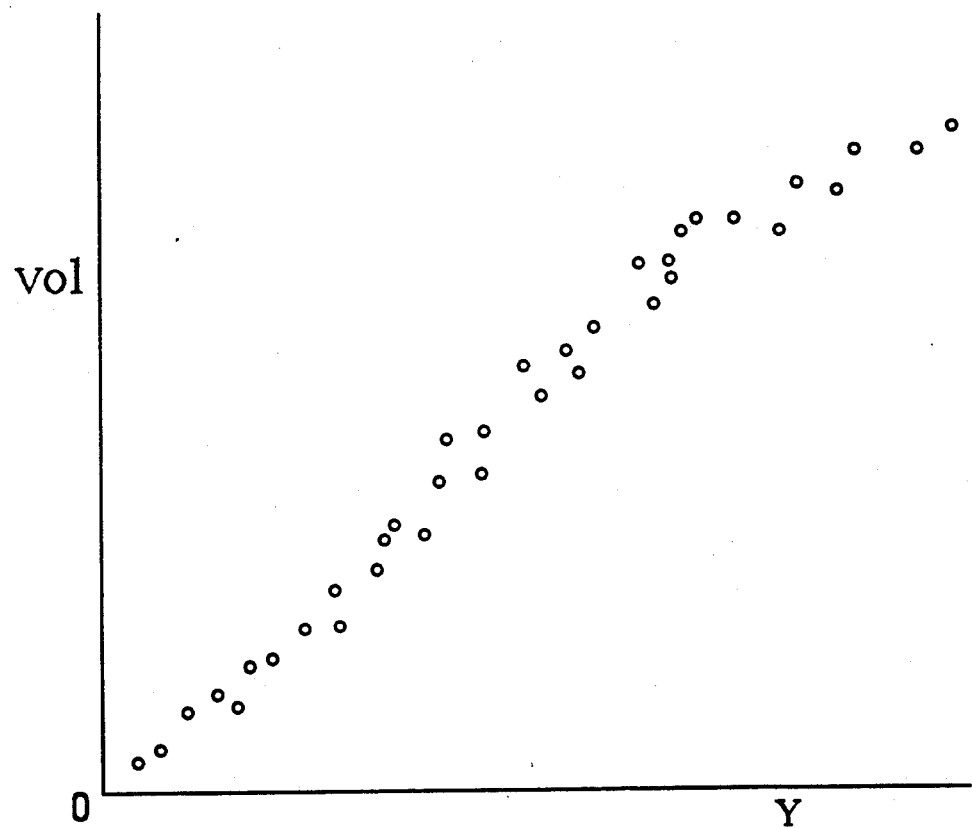
FIG. 13 is a graphic chart showing a relationship between the stroke Y of the passage 4 and an internal volume Vol of the passage 4.

In the second place, contents of feeding flow rate monitoring (86) will be described in conjunction with FIG. 7. A configuration of the passage 4 of the artificial heart 1 and an amount of blood (an inside volume of the passage 4) which fills the passage 4 exhibit one-to-one correspondence. Hence, the stroke width of the artificial heart 1 and the amount of blood in the passage 4 likewise show substantially one-to-one correspondence. The correspondence of the pump stroke to the inside volume of the passage is experimentally examined to obtain the data in detail. FIG. 13 shows the data obtained. Referring to FIG. 13, the axis of abscissa indicates a stroke width Y, while the axis of ordinate indicates a volume Vol of the suck 4. In the relationship between the stroke width and the volume in FIG. 13, Y can considerably accurately approximately to Vol by a linear or quadratic function. Stored in a program of the subroutine feeding flow rate monitoring (86) is a function of Vol=f(Y) in which to prescribe Y and Vol that are set on the basis of the data shown in FIG. 13. The operator inputs a coefficient of this function (an input of Vol=f(Y)) with the aid of the keyboard 41 in the before-stated step of reading an input by the operator and setting the data (54), and CPU 34 holds it in the internal register.

To start with, CPU 34 updates a content of a count register D up to a value greater by 1 than before (D1). The coefficient held in the internal register is set in the function of Vol=f(Y) in the program, and the stroke Y calculated in the step 82 is imparted to Y of the function. Then, Vn associated with the volume Vol of the suck 4 which corresponds thereto is calculated (D2). Next, there is calculated a volume variation quantity (a rate of variation) Vf (a flow rate during to=1/30 sec: an instantaneous flow rate) obtained by subtracting the volume $V_{n-1}$ computed last time from the volume Vn computed this time (D3). These volume variation quantities are written in time series to RAM 2 of the memory 42 and plot-displayed (D4) in a graph display region (*5) of a display region DA2 (FIG. 14a) of CRT 53. The plot display exhibits the instantaneous flow rates of the artificial heart 1.

The symbol Vf, which represents a discharge flow rate, is positive in a changeover from expansion to contraction but is negative in a changeover from the contraction to the expansion. In the negative state, Vf represents a suction flow rate. CPU 34 integrates the flow rates Vf for 2 seconds (60 times) (D5 through D9). A suction flow rate per minute is given by multiplying the integrated value by 30. The result is as follows:

$VmI = Vmi \times 30$

A discharge flow rate per minute is given by:

$VmO = Vmi \times 30$

The thus calculated values are written to RAM 2 of the memory 42 and displayed in a data display field (*6) of the display region DA2 of CRT 53. The integration is effected per 2 sec, and hence the representations of VmI and VmO are updated per 2 sec.

As discussed above, the discharge flow rate VmO and the suction flow rate VmI of the artificial heart 1 are measured with no addition of a separate measuring instrument such as an electromagnetic flow meter.

Note that the feeding flow rate is computed on the basis of the stroke Y in the foregoing step of feeding flow rate monitoring (86) but may also be obtained on the basis of the area S of the passage image. The one-to-one correspondence is exhibited with respect to the configuration of the passage 4 of the artificial heart 1 and the amount of the blood (an inside volume of the suck 4) with which the passage 4 is filled. Hence, the area S of an image (drawn with oblique lines in FIG. 9a) of the passage 4 and the blood quantity in the passage 4 similarly show substantially one-to-one correspondence. The correspondence of the passage image area to the passage inside volume is experimentally examined to obtain the data in detail. In the relationship between the area and the volume, S approximates to Vol by a linear or quadratic function expressed such as Vol=f(S). In the case of obtaining the flow rate by arithmetic based on the area S of the suck image, Vol=f(S) is employed for a calculation of the passage volume instead of the before-cited function of Vol=f(Y). Excepting this operation, the arithmetic and display operations, which are shown in FIG. 7, may similarly be executed.

Figure 8:
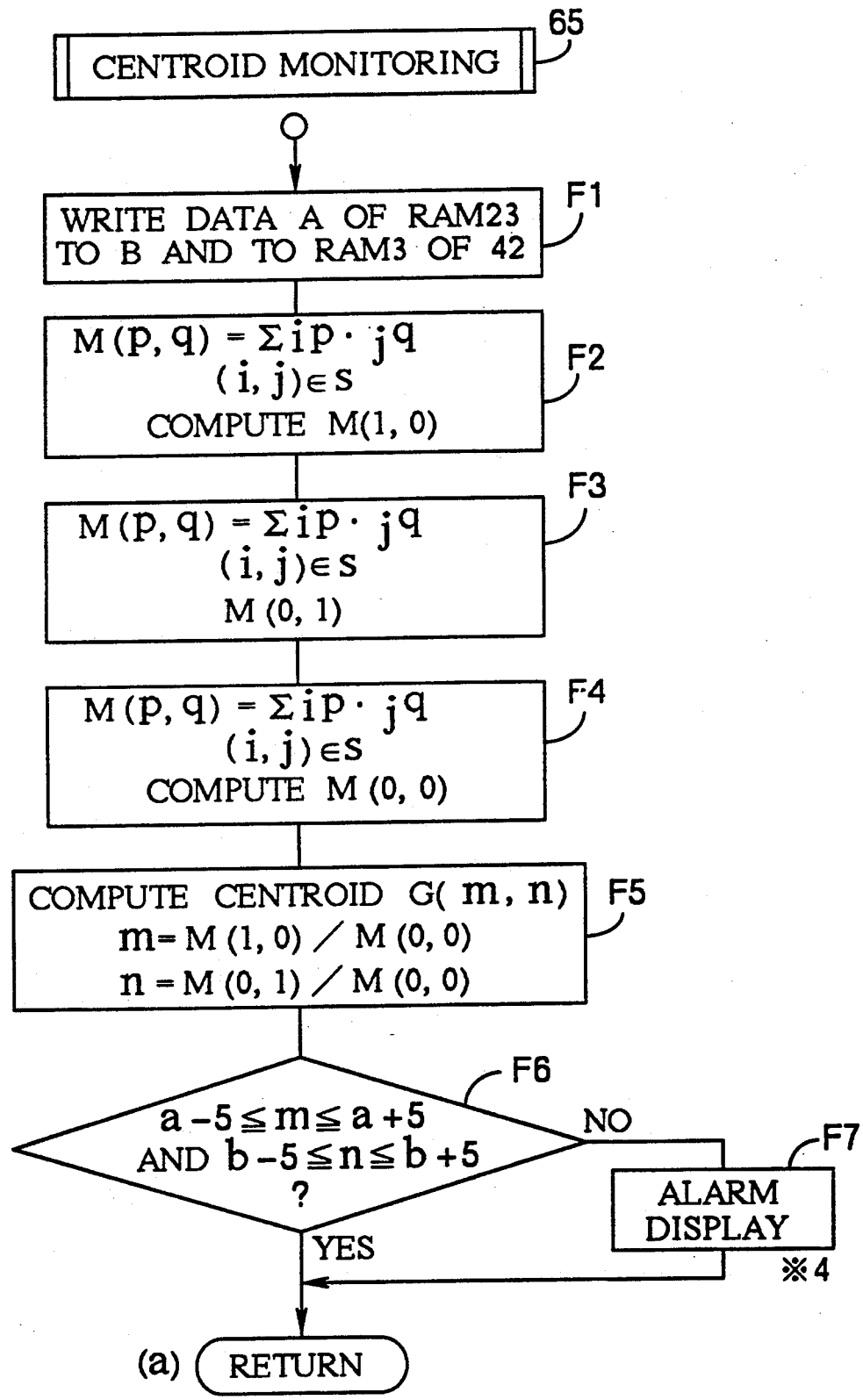

Turning next to FIG. 8, there is illustrated contents of centroid monitoring (65). The above-described steps of stopping time monitoring (83), stroke deflection monitoring (84), overpressure monitoring (85) and feeding flow rate monitoring (86) are executed by receiving interruption (80) which starts virtually at a cycle given by to=1/30 sec. Hence, those steps are executed virtually at the cycle of to=1/30 sec. In contrast, centroid monitoring (65) is executed by the main routine depicted in FIG. 3a.

The step of centroid monitoring (65) requires a relatively good deal of arithmetic time for computing the centroids, and therefore the execution is performed by the main routine so as not to give a virtual restraint to an executing time for one process.

As explained earlier, CPU 34 transmits the image take-in signals S2 to the image processing computer 17 at the cycle of to=1/30 sec. CPU 18 of the image processing computer 17, whenever it receives the signals S2, converts video signals, for one frame, of the CCD camera 9 into image data (gradation data) with the help of an A/D converter 26 and writes the image data to a frame memory 24. The image data are then binary-coded to obtain binary image signals for one frame which are to be written to RAM A of a frame memory 23. Therefore, the binary image signals for one frame of RAM A of the frame memory 23 are updated at a cycle to.

Assuming that one process (a centroid calculation of the passage image shown by the binary image signals for one frame) of centroid monitoring (65) is not finished within to, a target picture for calculating the centroid is varied in this case, resulting in an error of the centroid calculation. To cope with this, the binary image signals for one frame are written to RAM B of the frame memory 23 so that the target picture is not changed during one process. Based on the thus written binary image signals, the arithmetic operation of the centroid is effected.

To be more specific, CPU 34 at first gives DMA 32 of the image processing computer 17 an instruction to write the data of RAM A of the memory 23 to RAM B. Upon a completion of writing, CPU 34 issues an instruction to transfer the data of RAM A, which data are then written to RAM 2 (particularly to a memory region directed to a pixel display region *7 of the display region DA3 thereof). Image data marked with (+), to which blue display information is added, are additionally written in a specified centroidal position (a, b) which has previously been inputted and held in the step of reading an input by the operator and setting the data (54) and then displayed in the display region DA3 (particularly in the pixel display region *7 thereof) of CRT 53 (F1).

With this arrangement, the passage image and the blue (+) mark representing the specified centroidal position (a, b) are displayed in the pixel image display filed *7 of the display region DA3 of CRT 53.

CPU 34 causes an arithmetic CPU 35 to compute a moment M (1, 0), with respect to I-axis, of a two-dimensional distribution of a group of black pixels of the binary image signals of RAM B of the memory 42 on the assumption that a single piece of black pixel has a weight of 1 (F2). Similarly, CPU 35 computes a moment M (0, 1) with respect to a J-axis (F3) and an area M (0, 0) (F4). CPU 34 further causes CPU 35 to calculate a present position (m, n) of the centroid (F5). Note that in these arithmetic and calculating operations, CPU 34 instructs DMA 32 to transfer, to CPU 35, the binary image signals of necessary parts on the suck image picture (information of RAM B of the memory 23).

CPU 34, when acquiring the present centroidal position (m, n), additionally writes the (+) marked image data to which red display information is added in the present position (m, n) of the pixel display region *7 of the display region DA3 of RAM 3 of the memory 42, the image data being displayed in the display region DA3 (particularly in the pixel display region *7 thereof) of CRT 53) (F1).

Displayed in the pixel image display field *7 of the display region DA3 of CRT 53 are the suck image, the blue (+) mark indicating the specified centroidal position (a, b) and the red (+) mark representing the present centroidal position (m, n).

Subsequently, CPU 34 checks whether or not the present centroidal position (m, n), i.e., the red (+) mark is within +5 (pixel) both in a horizontal direction (H) and in a vertical direction (V) of the input centroidal position, viz., the blue (+) mark (F6). If deviated from that range, the buzzer 51 is energized, and a message (text information) of [passage abnormality. Inspect the artificial heart immediately.] is written to RAM 3 of the memory 42. This message is then displayed in an [ALARM] field (a text information display field) *4 of the display region DA3 of CRT 53 (F7).

The step of centroid monitoring (65) described above is repeatedly executed when internal timer interruption (70) and receiving interruption (80) are not yet executed by the main routine (FIG. 3a). Each time the repetition is carried out, there are updated the items, i.e., the passage image, the specified centroidal position (blue (+) mark) and the present centroidal position (red (+) mark) which are indicated in the pixel image display region *7 of the display region DA3 of CRT 53. If the present centroidal position (red (+) mark) deviates from a range of +5 pixels in the vertical direction (V) and in the horizontal direction (H) about the specified centroidal position (blue (+) mark), the buzzer 51 begins sounding, and a piece of text information saying [passage abnormality. Inspect the artificial heart immediately.] is displayed in the [ALARM] display field *4 of the display region DA3 of CRT 53.

A configuration and a thickness of the artificial heart 1 show a point symmetry virtually with respect to the centroidal position during the operation thereof. Since the passage 4 itself has a self-restoring property of configuration, the centroidal position of the passage 4 is kept substantially constant when the passage 4 is driven within a rated range under a non-failure condition.

Hence, if a large centroidal deviation takes place, there may be created such situations that the internal casing 2 comes off or is broken or deformed; or the passage 4 itself is deformed or broken; or the artificial heart driving module 10 is abnormally driven due to a deviation from a rated range or undergoes a failure. In any case, those conditions probably lead to accidents. The attention of the operator is aroused by a sound of the buzzer 51, and therefore the operator visually confirms a content of abnormality and a positional deviation or deformation of the passage 4. The operator immediately investigates a cause for the abnormality and can take a quick measure.

In accordance with the above-mentioned judgements of a variety of abnormalities and display processes, as illustrated in FIG. 14a, the multiple information indicating the operating states of the artificial heart 1 and the information on countermeasures are displayed on the display surface of CRT 53. It is to be noted that the items in the display region DA1 will be changed to those shown in FIGS. 14b and 14c as the case may be. Shown in a display region DA4 is a graphic display of 150 pieces of stroke Y data (one-dimensional array A) in time series (of samplings at a cycle to) of Y in a step A6 of stopping time monitoring (83) in connection with CPU 34. This graphic display corresponds to a graph depicted in the uppermost field of FIG. 9c.

Referring again to FIG. 1, the memory 42 may be defined as RAMs for storing the contents (message=-text data, graph and pixel image: pixel data) displayed on one picture of CRT 53. Among them, RAM 1 is set to store contents which are to be displayed in the display region DA1; RAM 2 stores those stored in the display region DA2; RAM 3 stores those displayed in the display region DA3; and RAM 4 stores those displayed in the display region DA4. Display forms (frame lines, display titles, items, etc.) are fixed. The information for displaying the forms is originally written to a floppy 50 and read to the data processing computer 33. The information is further written to RAM 45. The forms displayed in the display region DA1 are read from RAM 45 and written to RAM 1 of the memory 42 in conformity with judgments about the asynchronous/synchronous modes in stopping time monitoring (83) and judgments in the cases 0) through 3). The display forms of the display regions DA2 to DA4 are, since they are fixed, written to RAMs 2 through 4 of the memory 42 when being written to RAM 45.

As discussed above, the monitoring system according to the present invention includes; the dead center detecting means (9, 17 and 33) for detecting at least one of the top and bottom dead centers of the reversible operating means (4) of the medical pump (1); the dead center stopping time measuring means (33) for measuring a time for which the dead center detecting means (9, 17 and 33) continue to detect the dead centers; and the informing means (53) for informing the time measured by the dead center stopping time measuring means (33). The dead center stopping time measuring means (33) measures a stopping time of the top and/or bottom dead center, and the informing means (53) in turn informs this time value.

Based on this notification, the operator is capable of judging the availability or unavailability of an increase in the flow rate of the fluid fed out and abnormalities of the artificial heart.

The operator is able to recognize the availability or unavailability of the increase in the flow rate and the abnormalities without constant visual observation of the operating state of the artificial heart and presumptively grasping a situation on the basis of this visual observation, thereby reducing both troubles derived from a mistake of judgment by the operator and working burdens on the operator.

In accordance with the monitoring system of the present invention, the stroke detecting means (34) detects the strokes of the reversible operating means (4), while the passage detecting means (34) detects whether or not the strokes (Amax, Amin) detected by the stroke detecting means (34) traverse the predetermined strokes (SA, SB). If a result of the detection is negative, the informing means (53) gives the abnormality information. The informing means (3) automatically imparts the information indicating the abnormalities in such cases that the stagnation tends to occur due to a decrease in the flow rate when the stroke of the reversible operating means (4) diminishes, or the stroke of the reversible operating means (4) biases on the expanding or contracting side to facilitate the creation of local stagnation in the fluid space sectioned by the reversible operating means (4). Namely, there can be notified the biasing abnormality of the reversible operating means (4), which could not be automatically informed in the prior arts.

Hence, this facilitates the operator's judgment as to abnormalities in the medical pump, which conduces to reductions both in monitoring mistakes of the operator and in monitoring labors thereof.

In the monitoring system of the present invention, when the dead centers (Amax, Amin) of the stroke of the reversible operating means (4) which are detected by the dead center detecting means (9, 17 and 34) exceed the set limit points (Smax, Smin) due to the overexpanding and overcontracting movements of the reversible operating means (4) of the medical pump (1), the passage detecting means (34) detects the excessive value. The informing means (53) gives information on the abnormality in response to the foregoing detection. Hence, on the occasion of the overexpanding and overcontracting movements of the reversible operating means (4), the information indicating this abnormality is automatically notified, whereby the operator is able to know this abnormality without monitoring the reversible operating means (4) all the time. It is therefore possible to remarkably reduce both operator's labors for monitoring and a probability of causing judgment errors and mistakes in monitoring.

In accordance with the monitoring system of the present invention, since the imaging means (9) is in non-contact with the reversible operating (4) with no element added, the operating characteristic thereof do not change at all, and the durability does not decline. Based on the imaging means and the image processing techniques of nowadays, the image of the reversible operating means (4) can accurately be picked out, and the configurational parameter thereof can also be detected with accuracy. Therefore, the flow rate informed by the informing means (53) becomes precise.

Based on the monitoring system of the present invention, the informing means (53), when an abnormal deformation and an abnormal deflection appear before the reversible operating means (4) is ruptured, informs the abnormalities. Thus, the notification about the abnormalities is given before the reversible operating means (4) is broken. The operator visually inspect the medical pump with confirmation in response to the abnormality information. If abnormal, the operator can take a measure of replacing the pump; otherwise a driving pressure of the pump driving module may be adjusted, and a fault detection or replacement of the pump driving module may be effected. The operator does not have to monitor the operation of the medical pump all the time, thereby decreasing both working burdens and a possibility of causing the misjudgment and monitoring mistake.

Although the illustrative embodiment of the present invention has been described in detail with reference to the accompanying drawings, it is to be understood that the present invention is not limited to that precise embodiment. Various changes or modificaitons may be effected therein by one skilled in the art without departing from the scope and spirit of the invention.

What is claimed is:

1. A monitoring system for a medical pump having: a reversible operating means for compressing/expanding a space for accommodating a fluid; a discharge port and a suction port which communicate via a non-return valve with said fluid accommodating space; and reversible driving means for driving said reversible operating means, said system comprising:
an imaging means for generating image information by photographing said reversible operating means;
an image pick-out means for picking out an image of said reversible operating means from the image information generated by said imaging means;
a converting means for converting configurational parameters of the image of said reversible operating means which has been picked out by said image pick-out means into a volumetric capacity of a fluid accommodating space defined by said reversible operating means;
a variation rate detecting means for detecting a variation rate of the volumetric capacity converted by said converting means;
an integrating means for integrating the variation rate detected by said variation rate detecting means; and
an informing means for informing a value proportional to a value obtained by effecting the integration by said integrating means.

2. A monitoring system for a medical pump having: a reversible operating means for compressing/expanding a space for accommodating a fluid; a discharge port and a suction port which communicate via a non-return valve with said fluid accommodating space; and reversible driving means for driving said reversible operating means, said system comprising:
an imaging means for generating image information by photographing said reversible operating means;
an image pick-out means for picking out an image of said reversible operating means from the image information generated by said imaging means;
a centroid detecting means for calculating a centroidal position of the image of said reversible means which has been picked out by said image pick-out means;
a centroidal deviation detecting means for detecting whether or not the centroidal position calculated by said centroid detecting means falls within a set range; and
an informing means for giving corresponding information in response to a negative result of the detection by said centroidal deviation detecting means.

* * * * *